(12) United States Patent
Fuchigami

(10) Patent No.: US 12,260,960 B2
(45) Date of Patent: Mar. 25, 2025

(54) MEDICAL IMAGE PROCESSING APPARATUS, METHOD, AND PROGRAM

(71) Applicant: FUJIFILM Corporation, Tokyo (JP)

(72) Inventor: Takuya Fuchigami, Tokyo (JP)

(73) Assignee: FUJIFILM Corporation, Tokyo (JP)

(*) Notice: Subject to any disclaimer, the term of this patent is extended or adjusted under 35 U.S.C. 154(b) by 582 days.

(21) Appl. No.: 17/560,217

(22) Filed: Dec. 22, 2021

(65) Prior Publication Data

US 2022/0115136 A1 Apr. 14, 2022

Related U.S. Application Data

(63) Continuation of application No. PCT/JP2020/025401, filed on Jun. 26, 2020.

(30) Foreign Application Priority Data

Jun. 28, 2019 (JP) ................................. 2019-121016
May 15, 2020 (JP) ................................. 2020-086247

(51) Int. Cl.
G16H 50/20 (2018.01)
G06N 3/045 (2023.01)
G06T 7/00 (2017.01)
G16H 30/40 (2018.01)

(52) U.S. Cl.
CPC ............. *G16H 50/20* (2018.01); *G06N 3/045* (2023.01); *G06T 7/0012* (2013.01); *G16H 30/40* (2018.01); *G06T 2207/10072* (2013.01); *G06T 2207/20172* (2013.01); *G06T 2207/30016* (2013.01)

(58) Field of Classification Search
CPC ........ G16H 50/20; G16H 30/40; G16H 50/70; G06N 3/045; G06N 3/08; G06T 7/0012; G06T 2207/10072; G06T 2207/20172; G06T 2207/30016; G06T 2207/10081; G06T 2207/10088; G06T 2207/20021; G06T 2207/20084; G06T 7/68; A61B 5/055; A61B 6/03
See application file for complete search history.

(56) References Cited

U.S. PATENT DOCUMENTS

| 10,438,345 | B2* | 10/2019 | Wenzel | ................. G06T 7/0012 |
| 11,026,620 | B2* | 6/2021 | Kim | ..................... G06T 7/0014 |
| 2005/0113680 | A1 | 5/2005 | Ikeda et al. | |
| 2011/0116702 | A1 | 5/2011 | Bredno et al. | |

(Continued)

FOREIGN PATENT DOCUMENTS

| JP | 2005131011 | 5/2005 |
| JP | 2011167333 | 9/2011 |

(Continued)

OTHER PUBLICATIONS

"Office Action of Japan Counterpart Application" with English translation thereof, issued on Nov. 15, 2022, p. 1-p. 5.

(Continued)

*Primary Examiner* — Dhaval V Patel
(74) *Attorney, Agent, or Firm* — JCIPRNET

(57) ABSTRACT

A division unit divides an axisymmetric structure in a medical image including the structure into a plurality of predetermined regions. A reference line derivation unit derives a reference line of the structure on the basis of the plurality of divided regions.

13 Claims, 22 Drawing Sheets

(56) References Cited

U.S. PATENT DOCUMENTS

| | | | |
|---|---|---|---|
| 2012/0093385 | A1 | 4/2012 | Yokosawa et al. |
| 2017/0277977 | A1 | 9/2017 | Kitamura |
| 2018/0025255 | A1 | 1/2018 | Poole et al. |
| 2018/0143275 | A1 | 5/2018 | Sofka et al. |
| 2018/0204327 | A1* | 7/2018 | Matthews ............ A61B 5/7275 |
| 2018/0365824 | A1* | 12/2018 | Yuh ........................ G06T 7/136 |
| 2019/0267132 | A1 | 8/2019 | Fuchigami et al. |
| 2020/0090328 | A1 | 3/2020 | Takei et al. |

FOREIGN PATENT DOCUMENTS

| | | |
|---|---|---|
| JP | 2013085560 | 5/2013 |
| JP | 2017174039 | 9/2017 |
| JP | 2018011958 | 1/2018 |
| JP | 2019500110 | 1/2019 |
| JP | 2019149130 | 9/2019 |
| JP | 2020043927 | 3/2020 |
| KR | 20150034433 | 4/2015 |
| WO | 2010150783 | 12/2010 |
| WO | 2018156778 | 8/2018 |

OTHER PUBLICATIONS

Office Action of Japan Counterpart Application, with English translation thereof, issued on Aug. 30, 2022, pp. 1-6.
"International Search Report (Form PCT/ISA/210) of PCT/JP2020/025401," mailed on Sep. 29, 2020, with English translation thereof, pp. 1-6.
"Written Opinion of the International Searching Authority (Form PCT/ISA/237)" of PCT/JP2020/025401, mailed on Sep. 29, 2020, with English translation thereof, pp. 1-14.

* cited by examiner

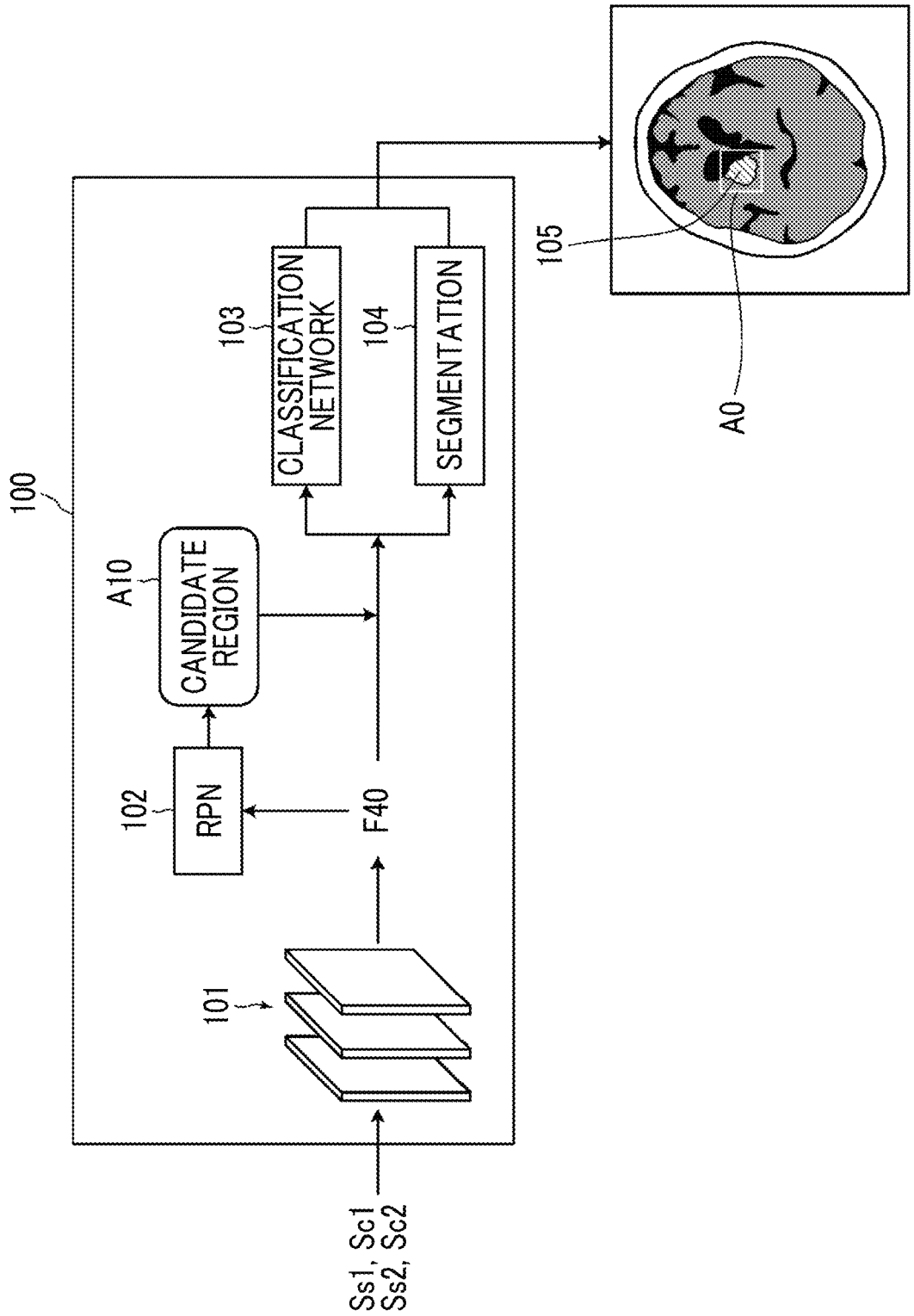

MEDICAL IMAGE PROCESSING APPARATUS, METHOD, AND PROGRAM

CROSS REFERENCE TO RELATED APPLICATIONS

The present application is a Continuation of PCT International Application No. PCT/JP2020/025401, filed on Jun. 26, 2020, which claims priority to Japanese Patent Application No. 2019-121016, filed on Jun. 28, 2019 and Japanese Patent Application No. 2020-086247, filed on May 15, 2020. Each application above is hereby expressly incorporated by reference, in its entirety, into the present application.

BACKGROUND

Technical Field

The present disclosure relates to a medical image processing apparatus, a medical image processing method, and a medical image processing program which derive a reference line in a medical image such as a brain image.

Related Art

In recent years, with advances in medical equipment such as computed tomography (CT) devices and magnetic resonance imaging (MRI) devices, an image diagnosis using high resolution medical images having higher quality can be performed. In particular, in a case where a target part is a brain, since it is possible to specify a disease region causing vascular disorders such as cerebral infarction and cerebral hemorrhage, by the image diagnosis using CT images and MRI images, an appropriate treatment can be performed on the basis of the specified result. In general, the disease region shows a higher signal value on the CT image or the MRI image as compared with the surrounding region. Therefore, it is possible to discriminate a disease region by interpreting the presence or absence of a region showing a higher signal value as compared with the surrounding region in the image diagnosis.

On the other hand, in a case where the medical image is a non-contrast CT image, in mild subarachnoid hemorrhage and cerebral infarction in the hyperacute phase, the contrast between the part where the disease is occurring and the surrounding part is unclear in many cases. Therefore, in a case of the image diagnosis, it is common practice to interpret the presence or absence of a disease region by comparing symmetrical regions of the brain in the medical image.

Various methods for detecting a disease region by comparing symmetrical regions have been proposed. For example, JP2018-011958A has proposed a method of discriminating the presence or absence of a disease region using a discriminator, which has performed machine learning, in a case where a combination of symmetrical regions in the medical image is input.

Further, in order to specify symmetrical regions, it is necessary to derive a midline in the brain as a reference line. Therefore, various methods for deriving the reference line in the brain have been proposed. For example, JP2019-500110A has proposed a method of deriving the reference line by applying an edge detection algorithm to the CT image of the brain, specifying eyeballs by Hough transform, and identifying a straight line segment within the midline of an intracranial space on the basis of a position of a center point of the eyeballs. Further, JP2011-167333A has proposed a method of specifying the reference line of the brain in the medical image by an operator's input.

However, in the method disclosed in JP2019-500110A, the reference line is specified using a structure such as an eyeball that is only one on each of the left and right sides. Therefore, the derived reference line is not very accurate. In particular, in a case where one or both eyes are injured due to an accident or disorder, in the method disclosed in JP2019-500110A, the reference line cannot be derived. Further, in the method disclosed in JP2011-167333A, since the reference line is specified by the operator's input, the burden on the operator is heavy.

SUMMARY OF THE INVENTION

The present disclosure is made in view of such circumstances, and an object thereof is to accurately derive the reference line of an axisymmetric structure such as the brain included in the medical image.

A medical image processing apparatus according to an aspect of the present disclosure comprises a division unit that divides an axisymmetric structure in a medical image including the structure into a plurality of predetermined regions; and a reference line derivation unit that derives a reference line of the structure on the basis of the plurality of divided regions.

The "axisymmetric structure" includes not only one structure that is axisymmetric in itself on the medical image, but also a pair or a plurality of pairs of structures present at axisymmetric positions on the medical image. For example, a brain has a basically (that is, anatomically) axisymmetric shape, and it is assumed that the brain is present in an axisymmetric manner, but the brain does not have a strictly axisymmetric shape, and may differ in size and shape between the left and right brains. Further, the kidneys are present in an anatomically axisymmetric manner, but may differ in size and shape between the left and right kidneys. Therefore, the axisymmetric structure" includes not only a structure forming a completely axisymmetric pair, but also an approximately axisymmetric structure and a structure assumed to be present in an axisymmetric manner.

The "reference line" is a line for dividing the axisymmetric structure in an axisymmetric manner. For example, a midline can be used as the reference line. The reference line also includes a line that divides the structure in an axisymmetric manner with some acceptable error.

The medical image processing apparatus according to the aspect of the present disclosure may further comprise a normalization unit that generates a normalized medical image by normalizing a position of the structure included in the medical image on the basis of the reference line.

The medical image processing apparatus according to the aspect of the present disclosure may further comprise an inversion unit that generates an inverted image by inverting the normalized medical image using the reference line as a reference; and a discrimination unit that discriminates a disease region of the structure using the normalized medical image and the inverted image.

In this case, the discrimination unit may have a discrimination model that outputs a discrimination result of the disease region of the structure in a case where the normalized medical image and the inverted image are input.

In the medical image processing apparatus according to the aspect of the present disclosure, in a case where the normalized medical image and the inverted image are input, the discrimination model may generate at least one feature map for the normalized medical image and the inverted image, and output the discrimination result of the disease region of the structure using the at least one feature map.

In the medical image processing apparatus according to the aspect of the present disclosure, the discrimination model may generate at least one feature map for each of the normalized medical image and the inverted image, and output the discrimination result of the disease region of the structure using the at least one feature map for the normalized medical image and the at least one feature map for the inverted image.

The medical image processing apparatus according to the aspect of the present disclosure may further comprise a discrimination unit that discriminates a disease region of the structure using the normalized medical image.

In this case, the discrimination unit may have a discrimination model that generates an inverted image of the normalized medical image and outputs a discrimination result of the disease region of the structure in a case where the normalized medical image is input.

In the medical image processing apparatus according to the aspect of the present disclosure, in a case where the normalized medical image is input, the discrimination model may generate at least one feature map from the normalized medical image, generate at least one inverted feature map obtained by inverting the at least one feature map using an axis of symmetry corresponding to the reference line as the reference, and output a discrimination result of the disease region of the structure using the at least one feature map and the inverted at least one feature map.

The term "discriminating" includes any of discriminating the position of the disease region in the medical image or discriminating the presence or absence of the disease region in the medical image.

In the medical image processing apparatus according to the aspect of the present disclosure, the discrimination model may consist of a neural network having at least one processing layer.

The medical image processing apparatus according to the aspect of the present disclosure may further comprise a display control unit that causes a display to display a discrimination result.

In the medical image processing apparatus according to the aspect of the present disclosure, the structure may be a brain, and the disease region may be an infarction region.

In the medical image processing apparatus according to the aspect of the present disclosure, the plurality of predetermined regions may be regions for deriving ASPECTS.

The "ASPECTS" is an abbreviation for the Alberta Stroke Program Early CT Score, and is a scoring method that quantifies the early CT sign of simple CT for cerebral infarction in the middle cerebral artery region. Specifically, the ASPECTS is a method in which, in a case where the medical image is the CT image, the middle cerebral artery region is divided into 10 regions in two typical sections (the basal ganglia level and the corona radiata level), the presence or absence of early ischemic changes is evaluated for each region, and a positive part is scored by a point deduction method. In a case where the medical image is an MRI image, especially a diffusion weighted image, the scoring is performed by dividing the middle cerebral artery region into 11 regions in two typical sections (the basal ganglia level and the corona radiata level). In the ASPECTS, the lower the score, the larger the area of the infarction region. The ASPECTS may be used to determine whether to apply intravenous tPA therapy, which is one of the treatment methods for cerebral infarction.

A medical image processing method according to another aspect of the present disclosure comprises dividing an axisymmetric structure in a medical image including the structure into a plurality of predetermined regions; and deriving a reference line of the structure on the basis of the plurality of divided regions.

The medical image processing method according to the aspect of the present disclosure may be provided as a program to be executed by a computer.

A medical image processing apparatus according to another aspect of the present disclosure comprises a memory that stores a command for execution of a computer; and a processor configured to execute the stored command, and the processor executes a process of dividing an axisymmetric structure in a medical image including the structure into a plurality of predetermined regions and deriving a reference line of the structure on the basis of the plurality of divided regions.

According to the present disclosure, it is possible to easily derive a reference line of a structure such as a brain included in a medical image.

BRIEF DESCRIPTION OF THE DRAWINGS

FIG. 31 is a schematic diagram illustrating a configuration of Mask R-CNN.

DETAILED DESCRIPTION

Figure 1:
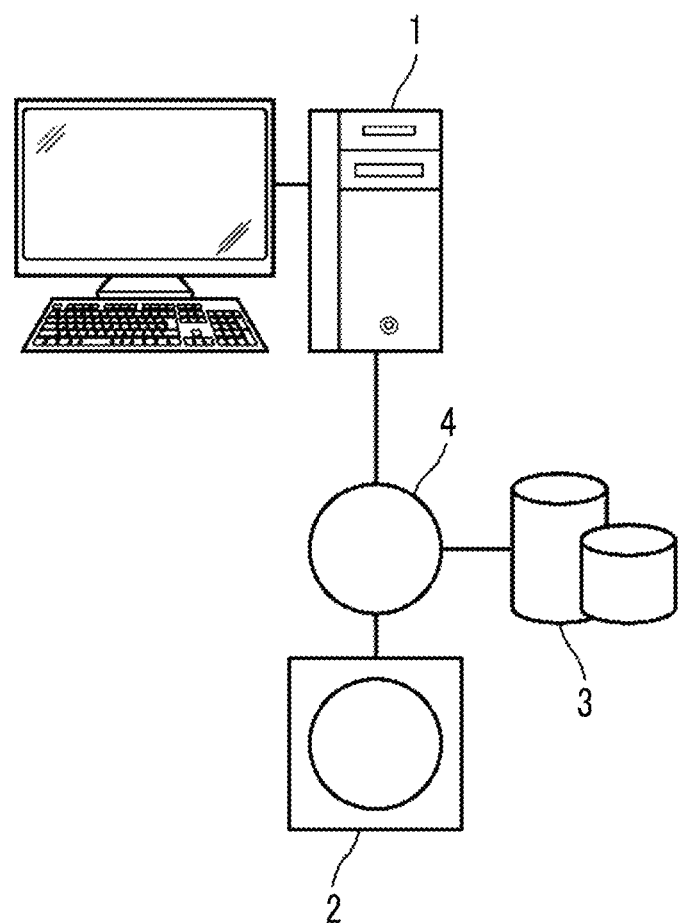
FIG. 1 is a hardware configuration diagram illustrating an outline of a diagnosis support system to which a medical image processing apparatus according to an embodiment of the present disclosure is applied.

Hereinafter, embodiments of the present disclosure will be described in detail with reference to the drawings. FIG. 1 is a hardware configuration diagram illustrating an outline of a diagnosis support system to which a medical image processing apparatus according to a first embodiment of the present disclosure is applied. As illustrated in FIG. 1, in the diagnosis support system, a medical image processing apparatus 1 according to the first embodiment, a three-dimensional image capturing device 2, and an image storage server 3 are connected via a network 4 in a communicable state.

The three-dimensional image capturing device 2 is a device that images a part as a diagnosis target of a subject to generate a three-dimensional image representing the part, and specifically, is a CT device, an MRI device, a positron emission tomography (PET) device, or the like. The three-dimensional image generated by the three-dimensional image capturing device 2 is transmitted to the image storage server 3 to be saved. In the present embodiment, the three-dimensional image capturing device 2 is a CT device, and a CT image of a head including the brain of the subject as a structure is generated as a three-dimensional brain image. The brain image includes a plurality of tomographic images. Further, the brain image and the tomographic image correspond to the medical image of the present disclosure.

The image storage server 3 is a computer that saves and manages various kinds of data, and comprises a large-capacity external storage device and software for database management. The image storage server 3 performs communication with other devices via the network 4 in a wired or wireless manner, and transmits and receives image data and the like. Specifically, the various kinds of data including image data of the brain image generated by the three-dimensional image capturing device 2 and image data of a standard division image representing the divided regions for the standard ASPECTS described below are acquired via the network, and are saved and managed in a recording medium such as a large-capacity external storage device. The image data storage format and the communication between the devices via the network 4 are based on a protocol such as Digital Imaging and Communication in Medicine (DICOM).

The medical image processing apparatus 1 is obtained by installing a medical image processing program of the first embodiment in one computer. The computer may be a workstation or a personal computer that a doctor performing a diagnosis operates directly, or a server computer connected to the workstation or personal computer via a network. The medical image processing program may be stored in a storage device of the server computer connected to the network or in a network storage in a state of being accessible from the outside, and may be downloaded and installed in a computer in response to a request. The medical image processing program is distributed by being recorded on a recording medium such as a digital versatile disc (DVD) or a compact disc read only memory (CD-ROM), and is installed to a computer from the recording medium.

Figure 2:
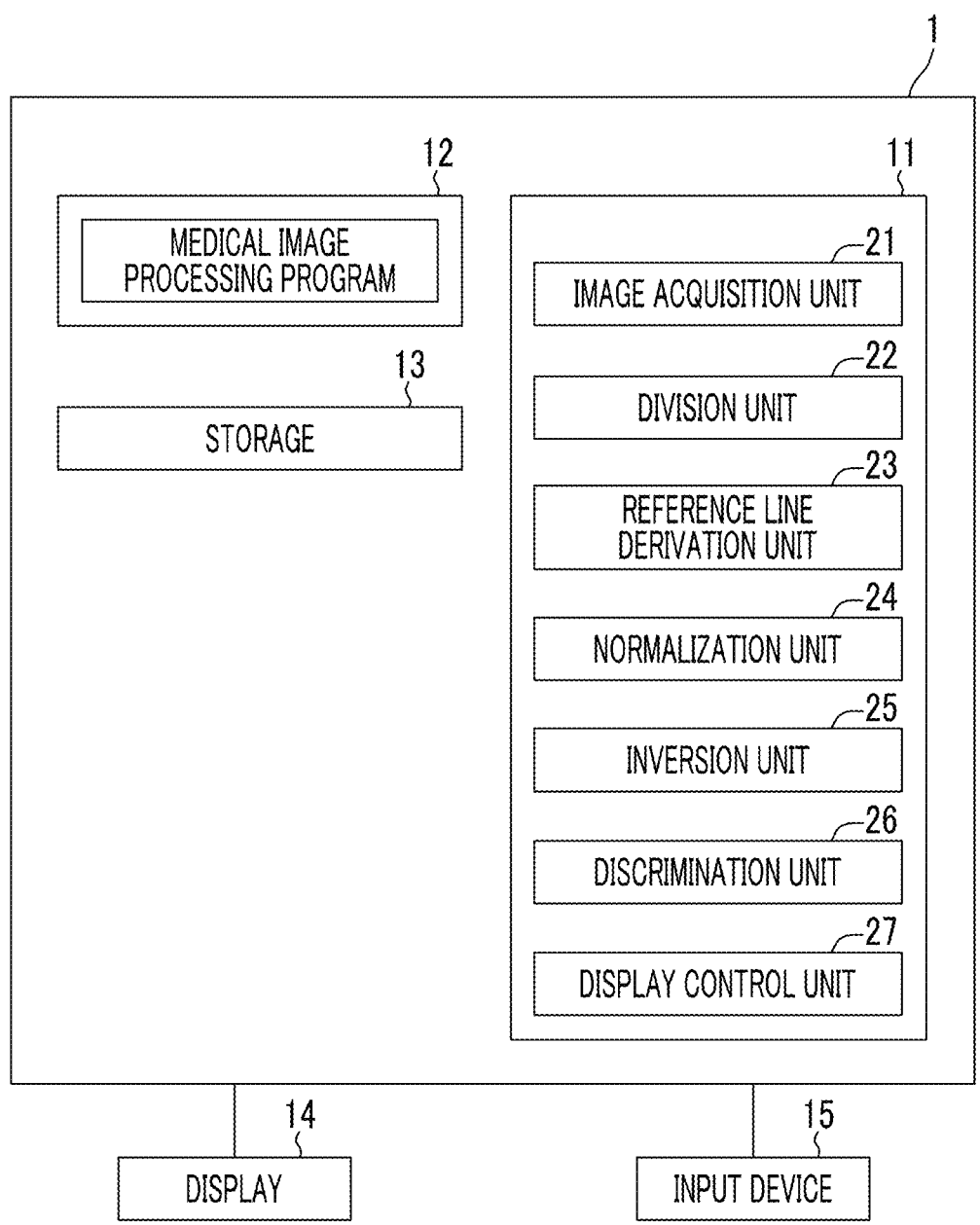
FIG. 2 is a diagram illustrating a schematic configuration of a medical image processing apparatus according to a first embodiment.

FIG. 2 is a diagram illustrating a schematic configuration of the medical image processing apparatus according to the first embodiment, which is realized by installing the medical image processing program in a computer. As illustrated in FIG. 2, the medical image processing apparatus 1 comprises a central processing unit (CPU) 11, a memory 12, and a storage 13 as a standard workstation configuration. In addition, a display 14 such as a liquid crystal display, and an input device 15 such as a keyboard and a mouse are connected to the medical image processing apparatus 1.

The storage 13 consists of a hard disk drive or the like, and various kinds of information including the brain images of the subject and information required for the process which are acquired from the image storage server 3 via the network 4 are stored.

In the memory 12, the medical image processing program is stored. The medical image processing program defines, as the process executed by the CPU 11, an image acquisition process of acquiring the medical image, a division process of dividing a structure in the medical image including an axisymmetric structure into a plurality of predetermined regions, a reference line derivation process of deriving a reference line of the structure on the basis of the plurality of divided regions, a normalization process of generating a normalized medical image by normalizing a position of the brain included in the medical image on the basis of the reference line, an inversion process of generating an inverted image obtained by inverting the normalized medical image using the reference line as a reference, a discrimination process of discriminating an abnormality of the structure using the normalized medical image and the inverted image, and a display control process of causing the display 14 to display the discrimination result. In the present embodiment, the medical image is the brain image, and the structure is the brain.

With the CPU 11 executing those processes according to the program, the computer functions as an image acquisition unit 21, a division unit 22, a reference line derivation unit 23, a normalization unit 24, an inversion unit 25, a discrimination unit 26, and a display control unit 27.

The image acquisition unit 21 acquires a brain image B0 of the subject from the image storage server 3. In a case where the brain image B0 is already stored in the storage 13, the image acquisition unit 21 may acquire the brain image B0 from the storage 13. In the present embodiment, the ASPECTS described later is derived. Therefore, in the present embodiment, only two tomographic images for deriving the ASPECTS may be acquired among three-dimensional brain images B0. In the present embodiment, the standard division image representing the divided regions for the standard ASPECTS described later is also acquired from the image storage server 3.

Figure 3:
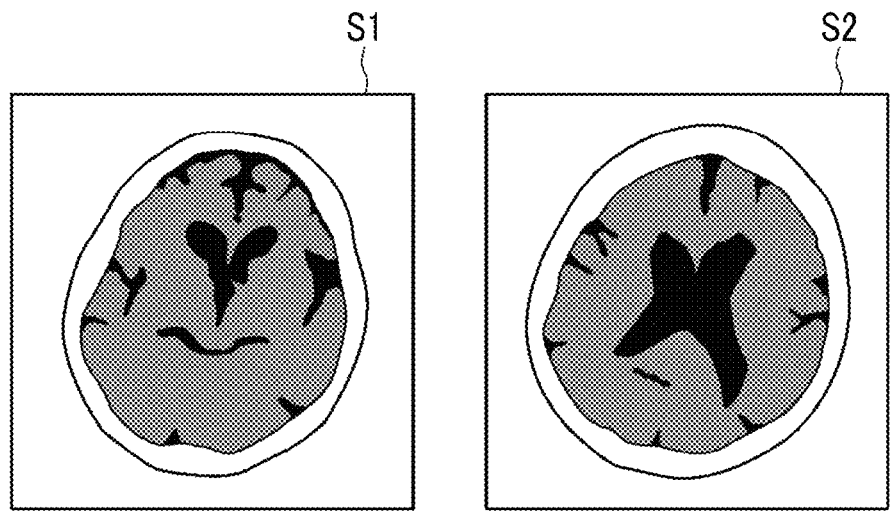
FIG. 3 is a diagram illustrating two tomographic images for deriving the ASPECTS.

FIG. 3 is a diagram illustrating two tomographic images for deriving the ASPECTS. Two tomographic images S1 and S2 illustrated in FIG. 3 respectively represent a tomographic plane at a basal ganglia level and a tomographic plane at a corona radiata level in a middle cerebral artery region of the brain. The head of a human body included in the two tomographic images S1 and S2 are not at the center thereof, and the midline that divides the brain into the left brain and the right brain is inclined with respect to the perpendicular line of the tomographic image. This is because patients with the cerebral infarction are often unconscious and often more urgent, so that the imaging is performed in a hurry while the patient is on a stretcher. Further, in a case where there is a disability in the cervical spine, it is better not to move the cervical spine, but the unconscious patient is unable to answer an inquiry about the disability in the cervical spine. In such a case, since the imaging is performed without moving the head, the midline is inclined with respect to the perpendicular line of the tomographic image. In the present embodiment, the midline of the brain is used as the reference line. The tomographic images S1 and S2 are images of the tomographic plane seen from the lower side of the human body to the parietal side, and the face is located on the upper side. Therefore, in the brain included in the tomographic images S1 and S2, the left brain is on the right side, and the right brain is on the left side.

The division unit 22 divides the structure in the medical image including the brain as the axisymmetric structure, into a plurality of predetermined regions. In the present embodiment, the medical images are two tomographic images for deriving the ASPECTS included in the brain image B0, the axisymmetric structure is the brain, and the brain is divided into a plurality of regions for deriving the ASPECTS.

Figure 4:
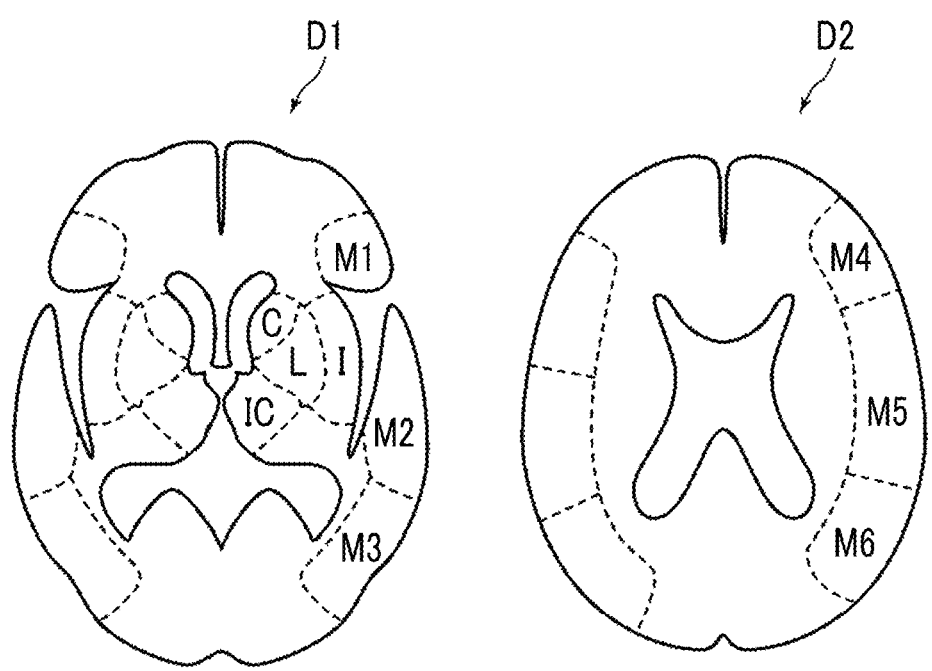
FIG. 4 is a diagram illustrating a standard division image representing divided regions of the ASPECTS.

FIG. 4 is a diagram illustrating the standard division image representing the divided regions of the ASPECTS. The ASPECTS is an abbreviation for the Alberta Stroke Program Early CT Score, and is a scoring method that quantifies the early CT sign of simple CT for cerebral infarction in the middle cerebral artery region. Specifically, the ASPECTS is a method in which, in a case where the medical image is the CT image, the middle cerebral artery region is divided into 10 regions in two typical sections (the basal ganglia level and the corona radiata level), the presence or absence of early ischemic changes is evaluated for each region, and a positive part is scored by a point deduction method. In a standard division image D1, each of the left and right middle cerebral artery regions in the tomographic plane at the basal ganglia level of the brain is divided into seven regions of C, I, L, IC, and M1 to M3. In a standard division image D2, each of the left and right middle cerebral artery regions in the tomographic plane at the corona radiata level is divided into three regions of M4 to M6. In FIG. 4, for the simplicity of the description, the reference numeral is illustrated only in the regions of the left brain.

Figure 5:
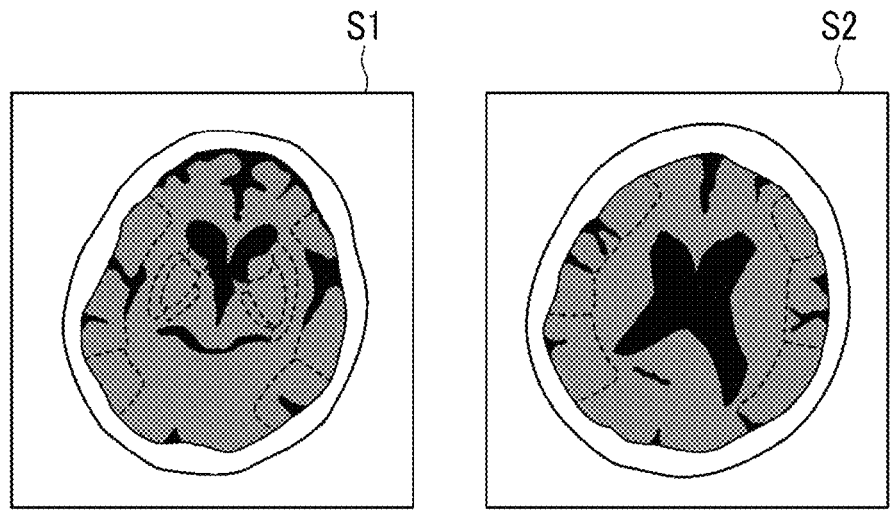
FIG. 5 is a diagram illustrating tomographic images divided into a plurality of regions.

In the present embodiment, the division unit 22 divides the tomographic image S1 at the basal ganglia level of the brain into seven regions of C, I, L, IC, and M1 to M3 of each of the left and right middle cerebral artery regions, and divides the tomographic image S2 at the corona radiata level into three regions of M4 to M6 of each of the left and right middle cerebral artery regions. For this purpose, the division unit 22 aligns the tomographic image S1 with the standard division image D1 illustrated in FIG. 4, and aligns the tomographic image S2 with the standard division image D2 illustrated in FIG. 4. Then, the divided regions in the aligned standard division images D1 and D2 are applied to the tomographic images S1 and S2, and the tomographic images S1 and S2 are divided into a plurality of regions. FIG. 5 is a diagram illustrating the tomographic images S1 and S2 divided into a plurality of regions.

The reference line derivation unit 23 derives a reference line of the brain on the basis of the plurality of divided regions in the tomographic images S1 and S2. In the present embodiment, the midline of the brain is the reference line. In order to derive the reference line, the reference line derivation unit 23 derives the centroid of each of the left brain and the right brain in the tomographic images S1 and S2. Since the process of deriving the reference line is the same for each of the tomographic images S1 and S2, only the derivation of the centroid for the tomographic image S2 will be described, and the derivation of the centroid for the tomographic image S1 will be omitted.

Figure 6:
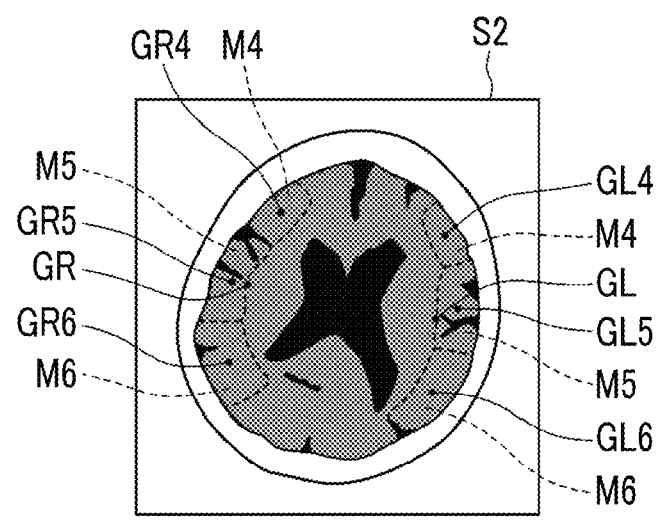
FIG. 6 is a diagram for describing the derivation of the centroid.

FIG. 6 is a diagram for describing the derivation of the centroid. As illustrated in FIG. 6, the reference line derivation unit 23 derives centroids GL4 to GL6 of the regions M4 to M6 of the left brain and centroids GR4 to GR6 of the regions M4 to M6 of the right brain of the tomographic image S2. Further, the reference line derivation unit 23 derives a centroid GL of the centroids GL4 to GL6 of the left brain, and a centroid GR of the centroids GR4 to GR6 of the right brain. The reference line derivation unit 23 may derive the centroid of the regions M4 to M6 in each of the left brain and the right brain as the centroid GL of the left brain and the centroid GR of the right brain without deriving the centroids GL4 to GL6 and the centroids GR4 to GR6.

Figure 7:
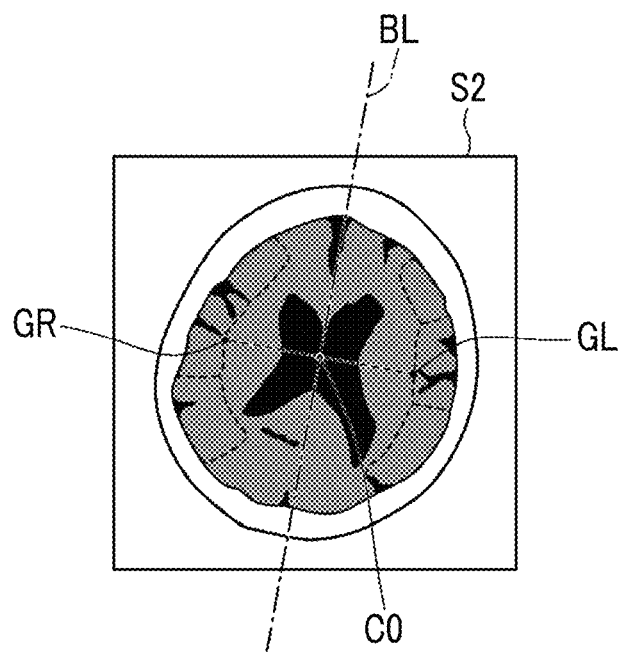
FIG. 7 is a diagram for describing the derivation of a reference line.

As illustrated in FIG. 7, the reference line derivation unit 23 derives a perpendicular bisector of the centroids GL and GR as a reference line BL. The reference line derivation unit 23 also derives a midpoint C0 of the centroids GL and GR. For the tomographic image S1, the reference line derivation unit 23 derives the centroid GL and GR of the left brain and the right brain, and derives a perpendicular bisector of the centroids GL and GR as the reference line BL.

Figure 8:
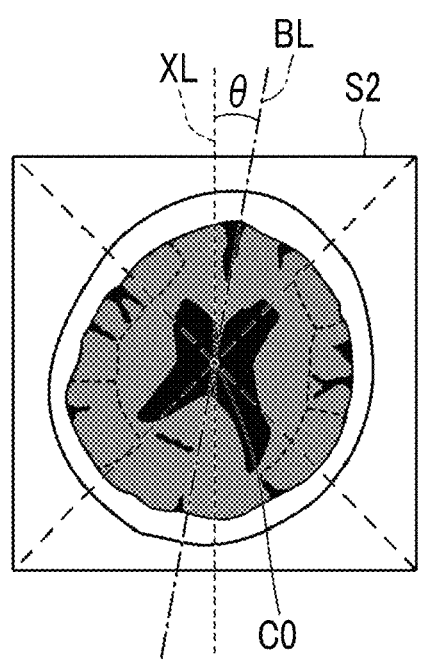
FIG. 8 is a diagram for describing normalization.
Figure 9:
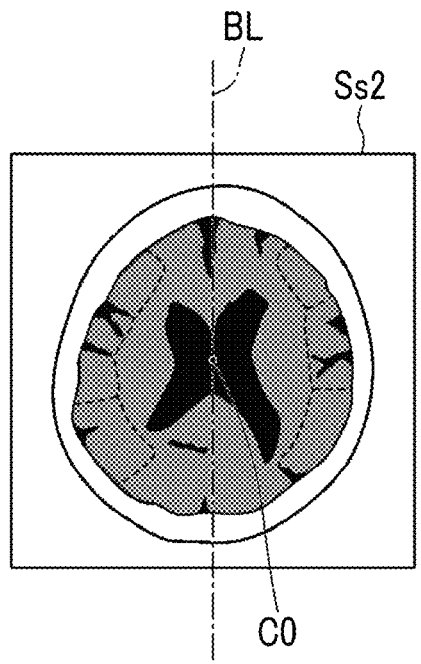
FIG. 9 is a diagram for describing normalization.

The normalization unit 24 normalizes the position of the brain included in the tomographic images S1 and S2. For this purpose, the normalization unit 24 translates the midpoint C0 of the centroids GL and GR of the brain so that the midpoint C0 coincides with the center of the tomographic images S1 and S2. FIG. 8 is a diagram illustrating the tomographic image S2 of which the midpoint C0 coincides with the center. In this state, the reference line BL is inclined by θ degrees clockwise with respect to a perpendicular line XL passing through the center of the tomographic image S2. Therefore, the normalization unit 24 rotates the brain included in the tomographic image S2 counterclockwise by θ degrees using the midpoint C0 as the center to cause the reference line BL to coincide with the perpendicular line XL of the tomographic image S2. In this manner, as illustrated in FIG. 9, the position of the brain in the tomographic image S2 is normalized. The normalization unit 24 normalizes the position of the brain of the tomographic image S1 in the same manner as the tomographic image S2. In the following description, the tomographic images S1 and S2 that are normalized are referred to as normalized tomographic images Ss1 and Ss2.

Figure 10:
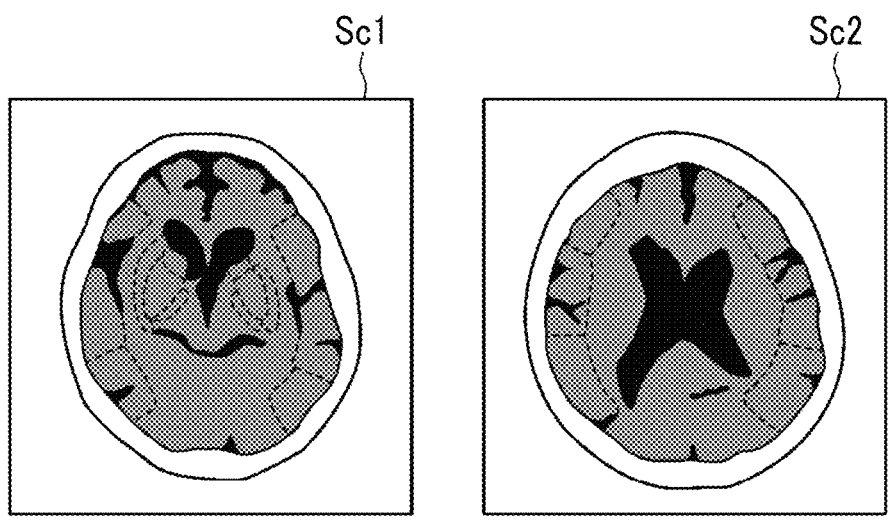
FIG. 10 is a diagram illustrating inverted tomographic images.

The inversion unit 25 generates inverted tomographic images obtained by inverting the normalized tomographic images Ss1 and Ss2 horizontally using the reference line BL as the reference. FIG. 10 is a diagram illustrating inverted tomographic images Sc1 and Sc2.

The discrimination unit 26 discriminates a disease region of the brain using each of the normalized tomographic images Ss1 and Ss2 and the inverted tomographic images Sc1 and Sc2. In the present embodiment, an infarction region is discriminated as the disease region of the brain. For this purpose, it is assumed that the discrimination unit 26 has a discrimination model consisting of a convolutional neural network (hereinafter, referred to as CNN) which is one of multi-layer neural networks in which a plurality of processing layers are hierarchically connected to each other and deep learning is performed.

Figure 11:
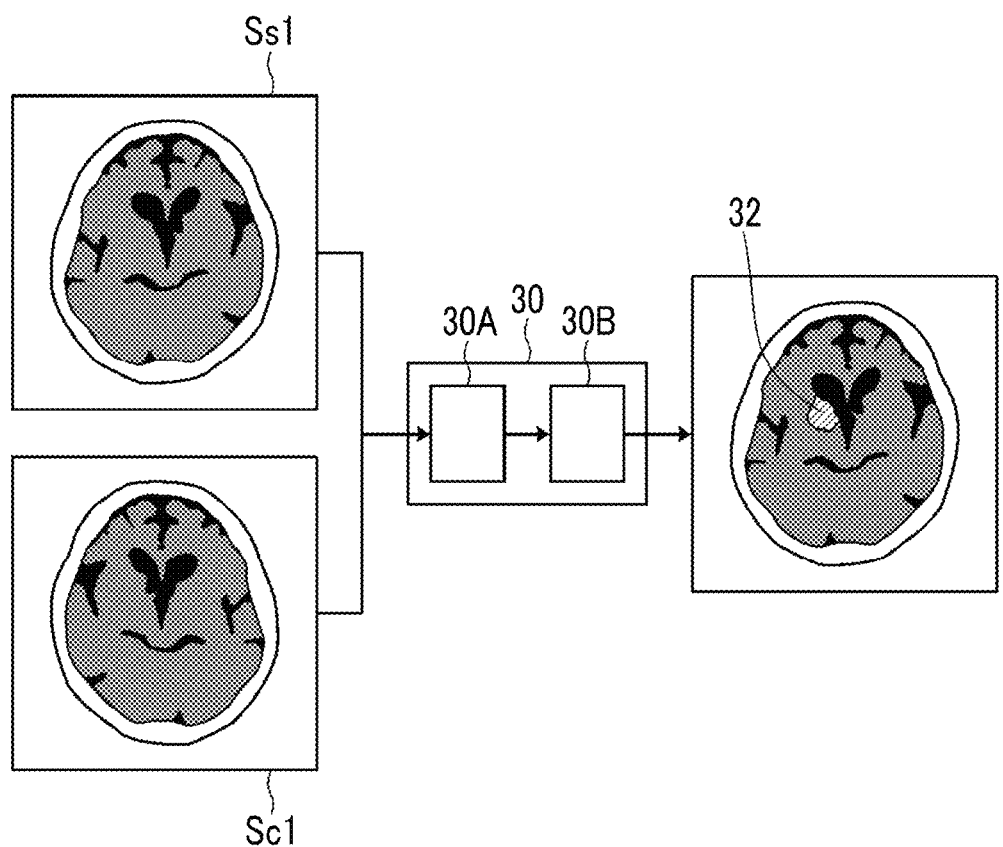
FIG. 11 is a conceptual diagram of a process performed by a discrimination model in the first embodiment.

FIG. 11 is a conceptual diagram illustrating a process performed by a discrimination model of the discrimination unit 26 together with a configuration of the discrimination model in the first embodiment. FIG. 11 illustrates only the normalized tomographic image Ss1 and the inverted tomographic image Sc1, but the same applies to the normalized tomographic image Ss2 and the inverted tomographic image Sc2. A discrimination model 30 illustrated in FIG. 11 consists of a CNN having an encoder 30A and a decoder 30B. The normalized tomographic image Ss1 and the inverted tomographic image Sc1 are input to the encoder 30A.

The encoder 30A has a plurality of processing layers including at least one of a convolutional layer or a pooling layer. In the present embodiment, the processing layers of the encoder 30A have both the convolutional layer and the pooling layer. The convolutional layer performs a convolution process using various kernels on the two input images (that is, the normalized tomographic image Ss1 and the inverted tomographic image Sc1, and the normalized tomographic image Ss2 and the inverted tomographic image Sc2) so as to detect the infarction region on the basis of the difference in pixel values of corresponding pixel positions, and outputs at least one feature map consisting of feature data obtained in the convolution process. The kernel has an n×n pixel size (for example, n=3), and a weight is set in each element. Specifically, a weight such as a differential filter for emphasizing the edge of the input image is set. The convolutional layer applies the kernel to the input image or the entire feature map output from the processing layer at the former stage while shifting the attention pixel of the kernel. Further, the convolutional layer applies an activation function such as a sigmoid function to a convolved value to output the feature map. Here, by using the difference in pixel values of the corresponding pixel positions of the two input images, the infarction region is detected using the symmetry using the reference line in the brain as the reference.

The pooling layer reduces the feature map by pooling the feature map output by the convolutional layer, and outputs the reduced feature map.

Then, the encoder 30A specifies the infarction region in the feature map by repeating the convolution and pooling.

The decoder 30B has a plurality of convolutional layers and upsampling layers. The convolutional layer performs the same process as the convolutional layer of the encoder 30A. The upsampling layer performs upsampling of the feature map to output an enlarged feature map. Then, the decoder 30B performs a process of classifying each pixel in the normalized tomographic images Ss1 and Ss2 into a pixel in the infarction region and a pixel that is not in the infarction region while increasing the resolution of the feature map output by the encoder 30A such that the feature map has a resolution of the normalized tomographic images Ss1 and Ss2. In this manner, a discrimination result of the infarction region in the normalized tomographic images Ss1 and Ss2 is output from the final layer of the decoder 30B which is the final layer of the discrimination model 30.

Figure 12:
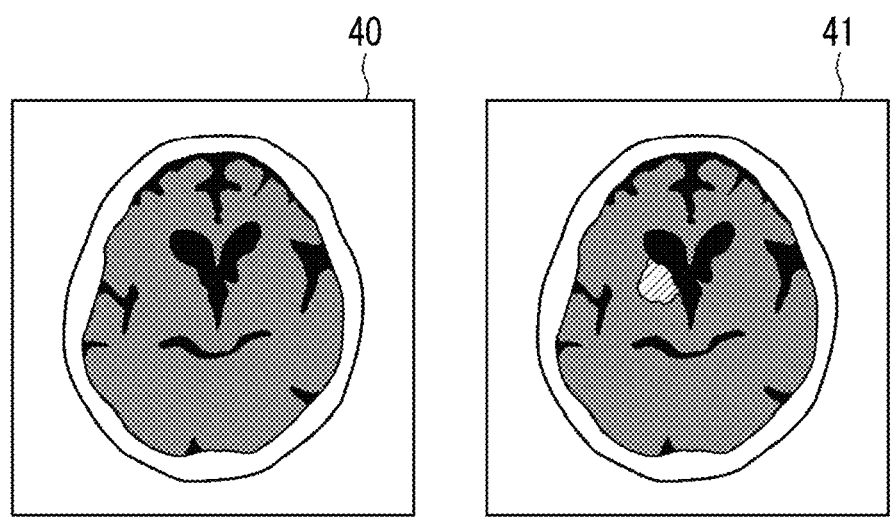
FIG. 12 is a diagram illustrating a learning image and ground truth data.

In a case where the normalized tomographic images Ss1 and Ss2 and the inverted tomographic images Sc1 and Sc2 are input, the discrimination model 30 performs learning so as to discriminate the infarction region in the normalized tomographic images Ss1 and Ss2. For the learning, as illustrated in FIG. 12, a large number of combinations of learning images 40 and ground truth data 41 in which the infarction regions in the learning images 40 are labeled are used.

In a case of the learning, an inverted image of the learning image 40 (referred to as a learning inverted image) is generated. Then, the learning image 40 and the learning inverted image are input to the CNN constituting the discrimination model 30, and the discrimination result of the infarction region is output from the CNN. The discrimination result of the infarction region is compared with the ground truth data 41, and the difference with the ground truth data is derived as a loss. Further, the learning of the CNN constituting the discrimination model 30 is performed using a large number of learning images 40 and the ground truth data 41 such that the loss is equal to or less than a predetermined threshold value. Specifically, the learning of the CNN is performed by repeatedly deriving the number of convolutional layers, the number of pooling layers, the kernel coefficient and the kernel size in the convolutional layer, and the like which constitute the CNN each time a loss is derived, such that the loss is equal to or less than the predetermined threshold value. In this manner, the discrimination model 30 is constructed which discriminates an infarction region 32 in the normalized tomographic images Ss1 and Ss2 in a case where the normalized tomographic images Ss1 and Ss2 and the inverted tomographic images Sc1 and Sc2 are input to the discrimination model 30.

Figure 13:
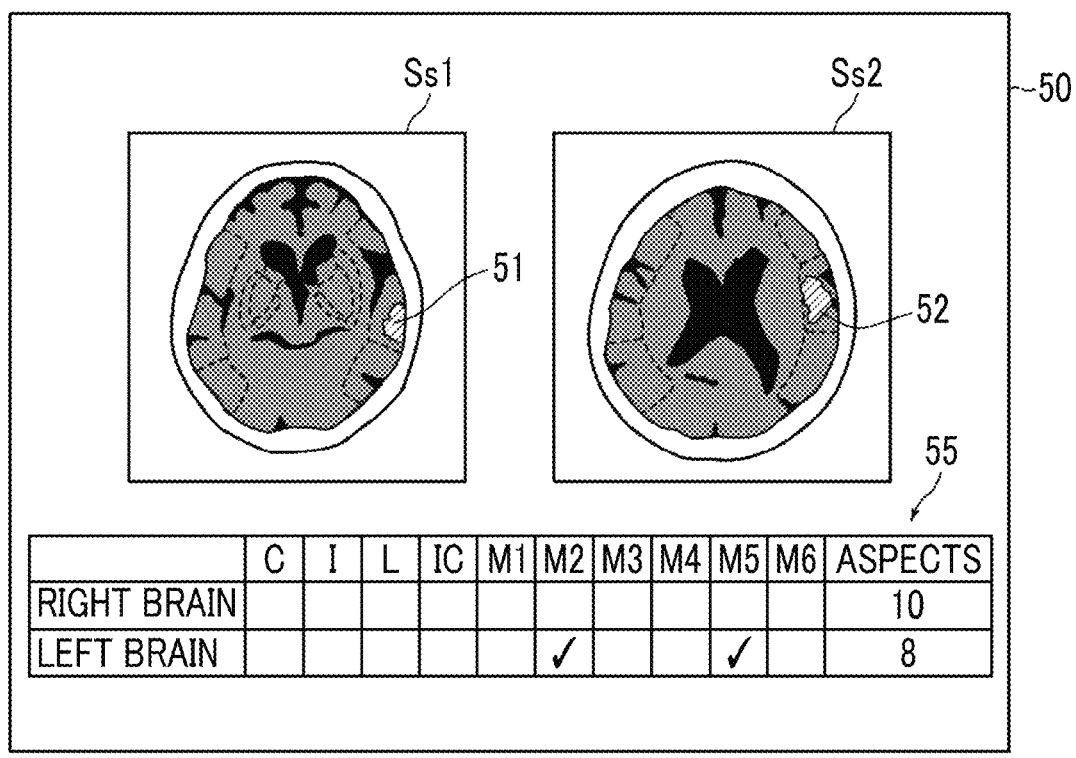
FIG. 13 is a diagram illustrating a discrimination result display screen.

The display control unit 27 causes the display 14 to display the discrimination result of the infarction region. FIG. 13 is a diagram illustrating a discrimination result display screen. As illustrated in FIG. 13, on a discrimination result display screen 50, the normalized tomographic images Ss1 and Ss2 are displayed. Further, labels 51 and 52 are assigned to the infarction regions discriminated in the normalized tomographic images Ss1 and Ss2. In the present embodiment, the ASPECTS 55 is displayed on the discrimination result display screen 50. The ASPECTS 55 includes a table in which a check mark is to be assigned to each of the 10 regions C, I, L, IC, and M1 to M6, for which the ASPECTS 55 is determined, in the normalized tomographic images Ss1 and Ss2. An operator determines the position of the infarction region, and assigns the check mark in the ASPECTS 55 on the discrimination result display screen 50. On the discrimination result display screen 50 illustrated in FIG. 13, the labels 51 and 52 specifying the infarction region are respectively assigned to the region M2 of the left brain of the normalized tomographic image Ss1 and the region M5 of the left brain of the normalized tomographic image Ss2. Therefore, the operator assigns the check mark to each of the regions M2 and M5 of the left brain. Since the infarction region is not included in the right brain, there is no check mark assigned in the table for the right brain. As a result, the ASPECTS of the right brain is 10, and the ASPECTS of the left brain is 8.

Figure 14:
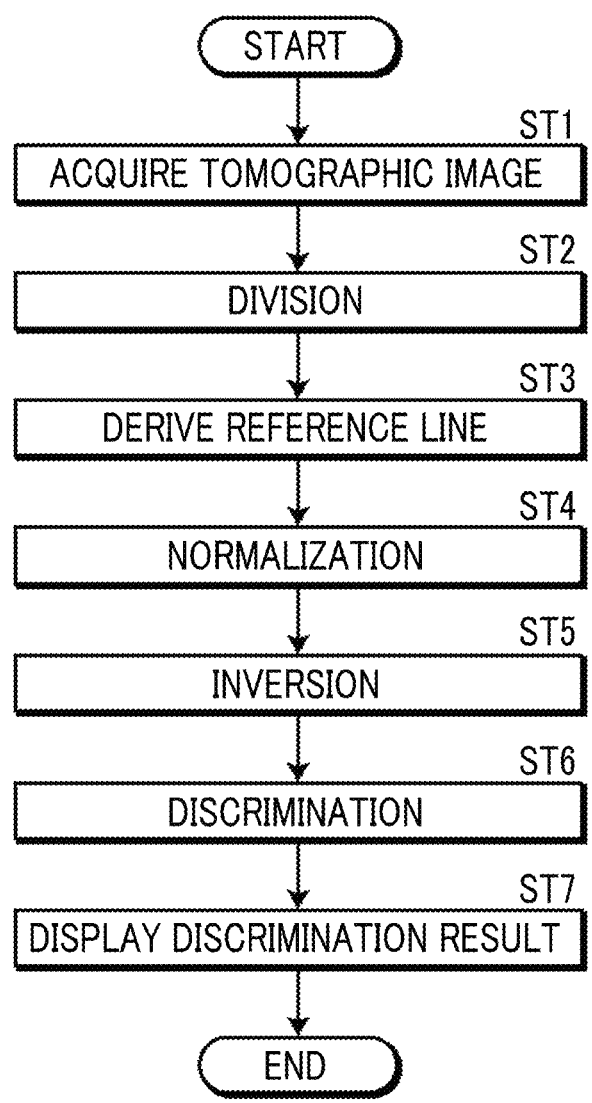
FIG. 14 is a flowchart illustrating a process performed in the first embodiment.

Next, the process performed in the first embodiment will be described. FIG. 14 is a flowchart illustrating the process performed in the first embodiment. First, the image acquisition unit 21 acquires the tomographic images S1 and S2 included in the brain image B0 (Step ST1). Next, the division unit 22 divides the brain included in the tomographic images S1 and S2 into a plurality of predetermined regions (Step ST2). The reference line derivation unit 23 derives the reference line BL of the brain on the basis of the plurality of divided regions in the tomographic images S1 and S2 (Step ST3). Further, the normalization unit 24 normalizes the position of the brain included in the tomographic images S1 and S2 (Step ST4). In this manner, the normalized tomographic images Ss1 and Ss2 are generated. Next, the inversion unit 25 inverts the normalized tomographic images Ss1 and Ss2 horizontally using the reference line BL as the reference (Step ST5). In this manner, the inverted tomographic images Sc1 and Sc2 are generated.

The discrimination unit 26 discriminates the disease region of the brain using the normalized tomographic images Ss1 and Ss2 and the inverted tomographic images Sc1 and Sc2 (Step ST6). Then, the display control unit 27 causes the display 14 to display the discrimination result (Step ST7), and the process is ended.

In this manner, in the first embodiment, the structure in the medical image including the axisymmetric structure is divided into the plurality of predetermined regions, and the reference line of the structure is derived on the basis of the plurality of divided regions. Specifically, each of the left brain and the right brain included in the tomographic images S1 and S2 is divided into 10 regions based on the ASPECTS, and the reference line BL is derived on the basis of the plurality of divided regions. In this manner, in the present embodiment, since the reference line BL is derived on the basis of the plurality of regions in the brain, the reference line can be derived more reliably and accurately as compared with the method of deriving the midline using only the eyeballs as in the method disclosed in JP2019-500110A. Further, the burden on the operator can also be reduced as compared with the method disclosed in JP2011-167333A.

Since the position of the brain included in the tomographic images S1 and S2 is normalized on the basis of the derived reference line BL, the normalized tomographic images Ss1 and Ss2 in which the position of the brain is more accurately normalized can be generated.

Since the normalized tomographic images Ss1 and Ss2 which are normalized on the basis of the derived reference line BL are inverted, the inverted tomographic images Sc1 and Sc2 that have been more accurately inverted horizontally can be generated.

Figure 15:
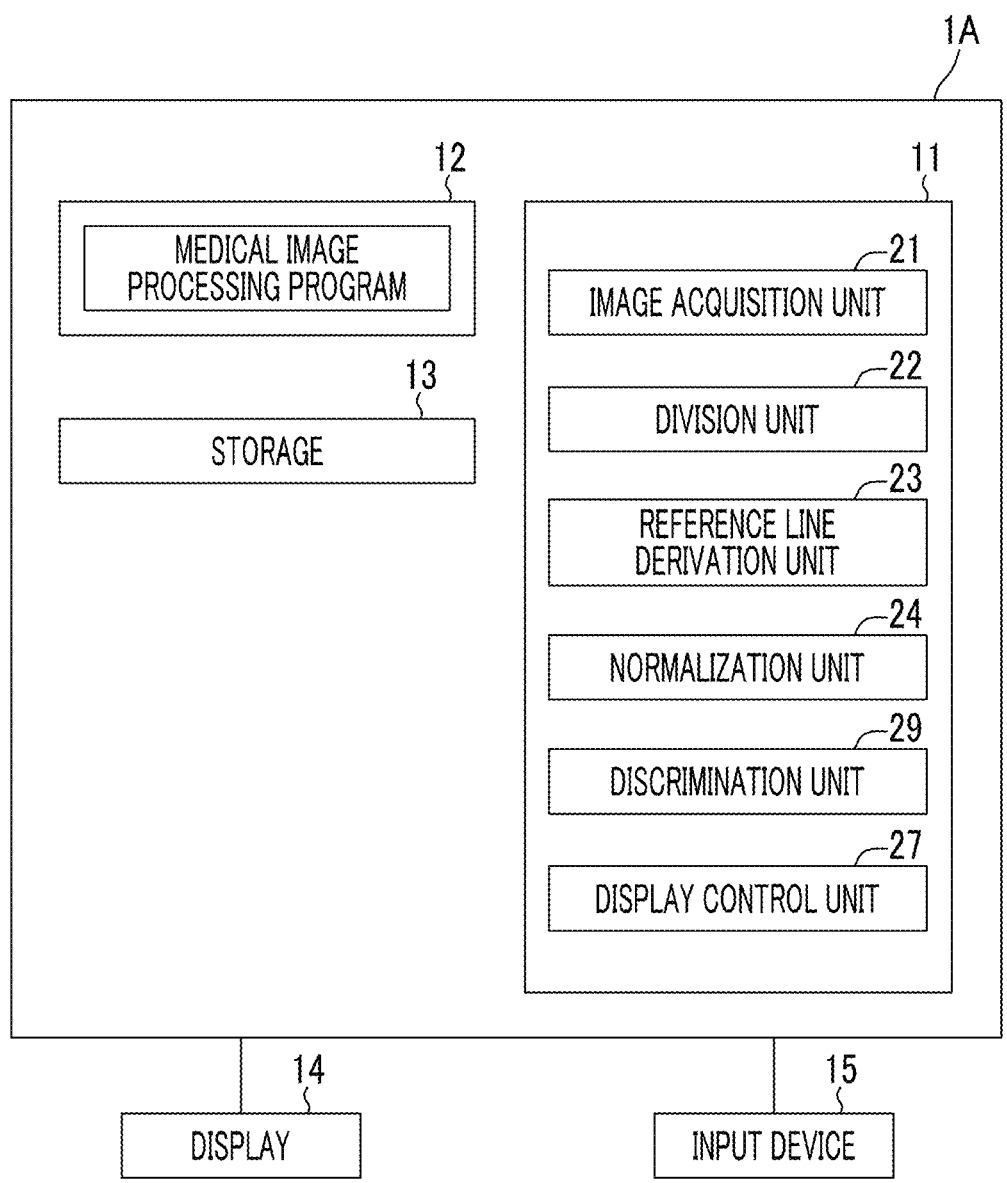
FIG. 15 is a diagram illustrating a schematic configuration of a medical image processing apparatus according to a second embodiment.

Hereinafter, a second embodiment of the present disclosure will be described. FIG. 15 is a diagram illustrating a schematic configuration of a medical image processing apparatus according to the second embodiment of the present disclosure. In FIG. 15, the same reference numerals are given to the same configurations as those in FIG. 2, and the detailed description thereof will be omitted. A medical image processing apparatus 1A according to the second embodiment is different from the first embodiment in that the medical image processing apparatus 1A comprises a discrimination unit 29 that discriminates an abnormality of the brain using the normalized tomographic images Ss1 and Ss2, instead of the inversion unit 25 and the discrimination unit 26 of the medical image processing apparatus 1 in the first embodiment.

Figure 16:
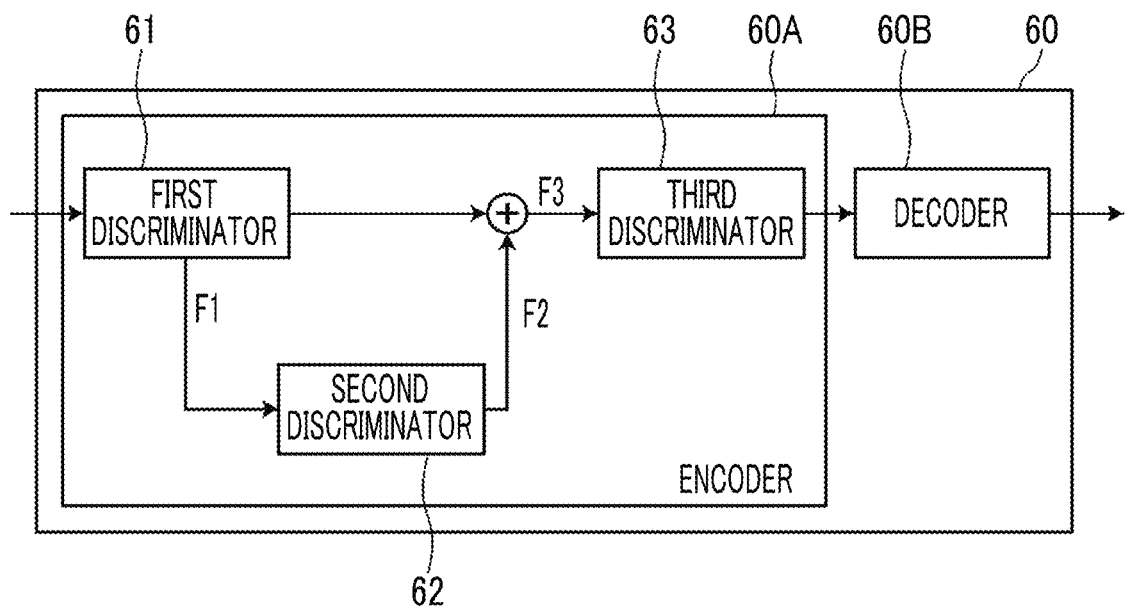
FIG. 16 is a schematic block diagram illustrating a configuration of a discrimination model in the second embodiment.

FIG. 16 is a schematic block diagram illustrating a configuration of a discrimination model of the discrimination unit 29 in the second embodiment. A discrimination model 60 of the discrimination unit 29 illustrated in FIG. 16 has an encoder 60A and a decoder 60B. The discrimination model 60 in the second embodiment performs learning in the same manner as the discrimination model 30, by using a large number of learning images and ground truth data such that the discrimination result of the infarction region in the normalized tomographic images Ss1 and Ss2 is output in a case where the normalized tomographic images Ss1 and Ss2 are input, but is different from the discrimination model 30 in that the inverted tomographic images Sc1 and Sc2 are internally generated. For this purpose, the encoder 60A has a first discriminator 61, a second discriminator 62, and a third discriminator 63.

Figure 17:
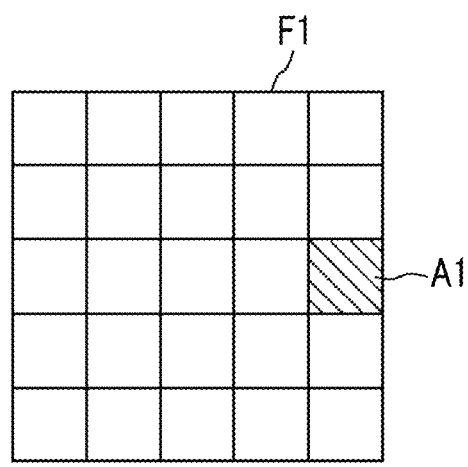
FIG. 17 is a diagram illustrating a feature map.

The first discriminator 61 consists of a convolutional neural network having a plurality of processing layers including at least one of the convolutional layer or the pooling layer, and performs at least one of the convolution process or the pooling process in each processing layer to output a feature map F1. FIG. 17 is a diagram illustrating an example of the feature map F1 output from the first discriminator 61. In FIG. 17, for the simplicity of the description, the resolution of the feature map F1 is set to 5×5 pixels, but the disclosure is not limited thereto. Here, in a case where the normalized tomographic image Ss1 includes the infarction region at the same position as the normalized tomographic image Ss1 illustrated in FIG. 13, the resolution of the feature map F1 is 5×5 pixels, and a feature A1 is included at a position corresponding to the infarction region of the normalized tomographic image Ss1 as illustrated in FIG. 17.

Figure 18:
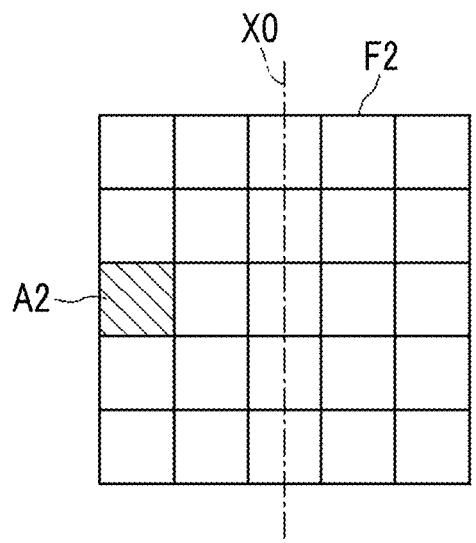
FIG. 18 is a diagram illustrating an inverted feature map.

The second discriminator 62 generates an inverted feature map F2 by inverting the feature map F1, which is output by the first discriminator 61, using the axis of symmetry thereof as the reference. The axis of symmetry corresponds to the reference line BL output by the reference line derivation unit 23. For this purpose, the processing layer of the second discriminator 62 performs the convolution process of inverting the feature map F1 using the axis of symmetry as the reference. FIG. 18 is a diagram illustrating the inverted feature map. As illustrated in FIG. 18, the inverted feature map F2 is generated by inverting the feature map F1 illustrated in FIG. 17 horizontally using an axis of symmetry X0 as the reference. Therefore, a feature A1 of the feature map F1 is present as the feature A2 of the inverted feature map F2. The second discriminator 62 may have only one processing layer or may have a plurality of processing layers as long as the inverted feature map F2 can be generated from the feature map F1.

Figure 19:
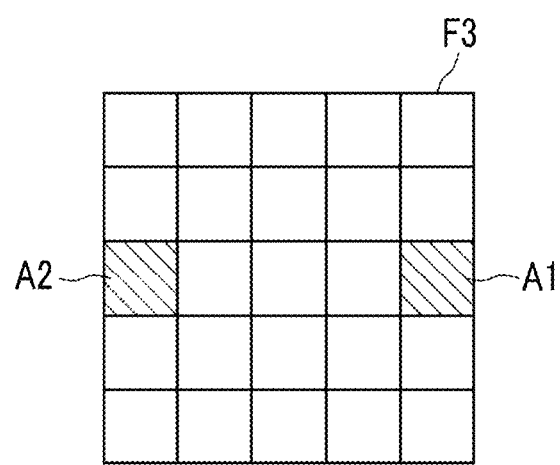
FIG. 19 is a diagram illustrating a superimposition map.

The third discriminator 63 consists of a convolutional neural network having a plurality of processing layers including at least one of the convolutional layer or the pooling layer, and superimposes the feature map F1 output by the first discriminator 61 and the inverted feature map F2 output by the second discriminator 62 on each other to generate a superimposition map in the first processing layer. In FIG. 16, for the description of superimposition, the first processing layer of the third discriminator 63 is indicated by a positive sign separately from the third discriminator 63. FIG. 19 is a diagram illustrating the superimposition map. The third discriminator 63 discriminates the infarction region in the normalized tomographic images Ss1 and Ss2 on the basis of a superimposition map F3. Specifically, a process of specifying the infarction region is performed on the basis of the superimposition map F3.

The decoder 60B performs a process of classifying each pixel in the normalized tomographic images Ss1 and Ss2 into a pixel in the infarction region and a pixel that is not in the infarction region while increasing the resolution of the feature map, in which the infarction region is specified, such that the feature map has a resolution of the normalized tomographic images Ss1 and Ss2. In this manner, a discrimination result of the infarction region in the normalized tomographic images Ss1 and Ss2 is output from the final layer of the decoder 60B which is the final layer of the discrimination model 60.

Figure 20:
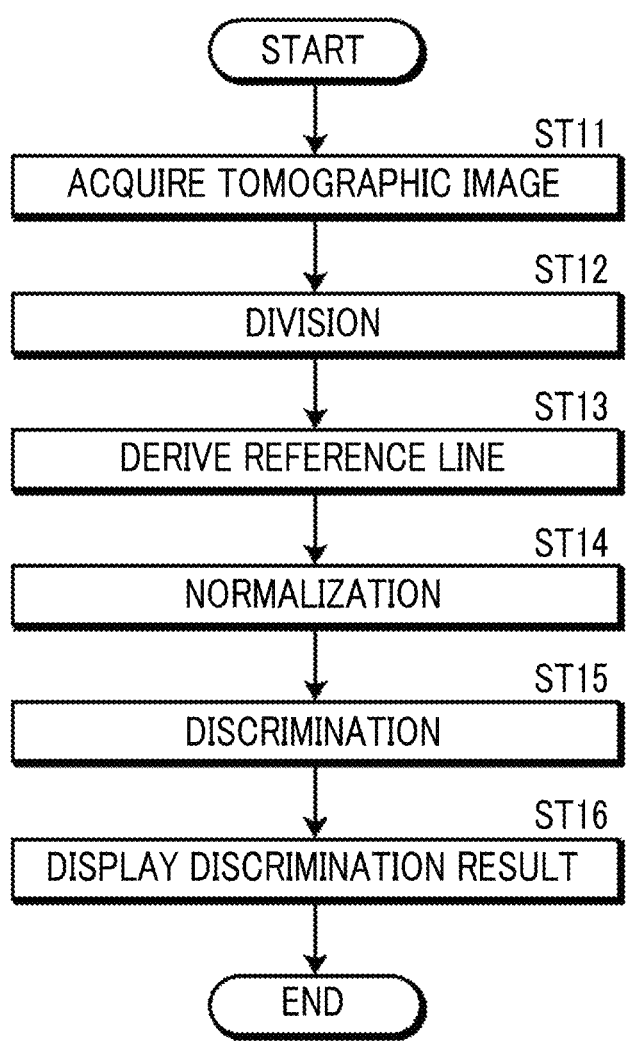
FIG. 20 is a flowchart illustrating a process performed in the second embodiment.

Next, the process performed in the second embodiment will be described. FIG. 20 is a flowchart illustrating the process performed in the second embodiment. First, the image acquisition unit 21 acquires the tomographic images S1 and S2 included in the brain image B0 (Step ST11). Next, the division unit 22 divides the brain included in the tomographic images S1 and S2 into a plurality of predetermined regions (Step ST12). The reference line derivation unit 23 derives the reference line BL of the brain on the basis of the plurality of divided regions in the tomographic images S1 and S2 (Step ST13). Further, the normalization unit 24 normalizes the position of the brain included in the tomographic images S1 and S2 (Step ST14). In this manner, the normalized tomographic images Ss1 and Ss2 are generated.

The discrimination unit 29 discriminates the disease region of the brain using the normalized tomographic images Ss1 and Ss2 (Step ST15). Then, the display control unit 27 causes the display 14 to display the discrimination result (Step ST16), and the process is ended.

Hereinafter, a third embodiment of the present disclosure will be described. Since a configuration of a medical image processing apparatus according to the third embodiment of the present disclosure is the same as that of the medical image processing apparatus 1 according to the first embodiment illustrated in FIG. 2, except that a configuration of the discrimination model of the discrimination unit 26 is different, the detailed description for the configuration is omitted.

Figure 21:
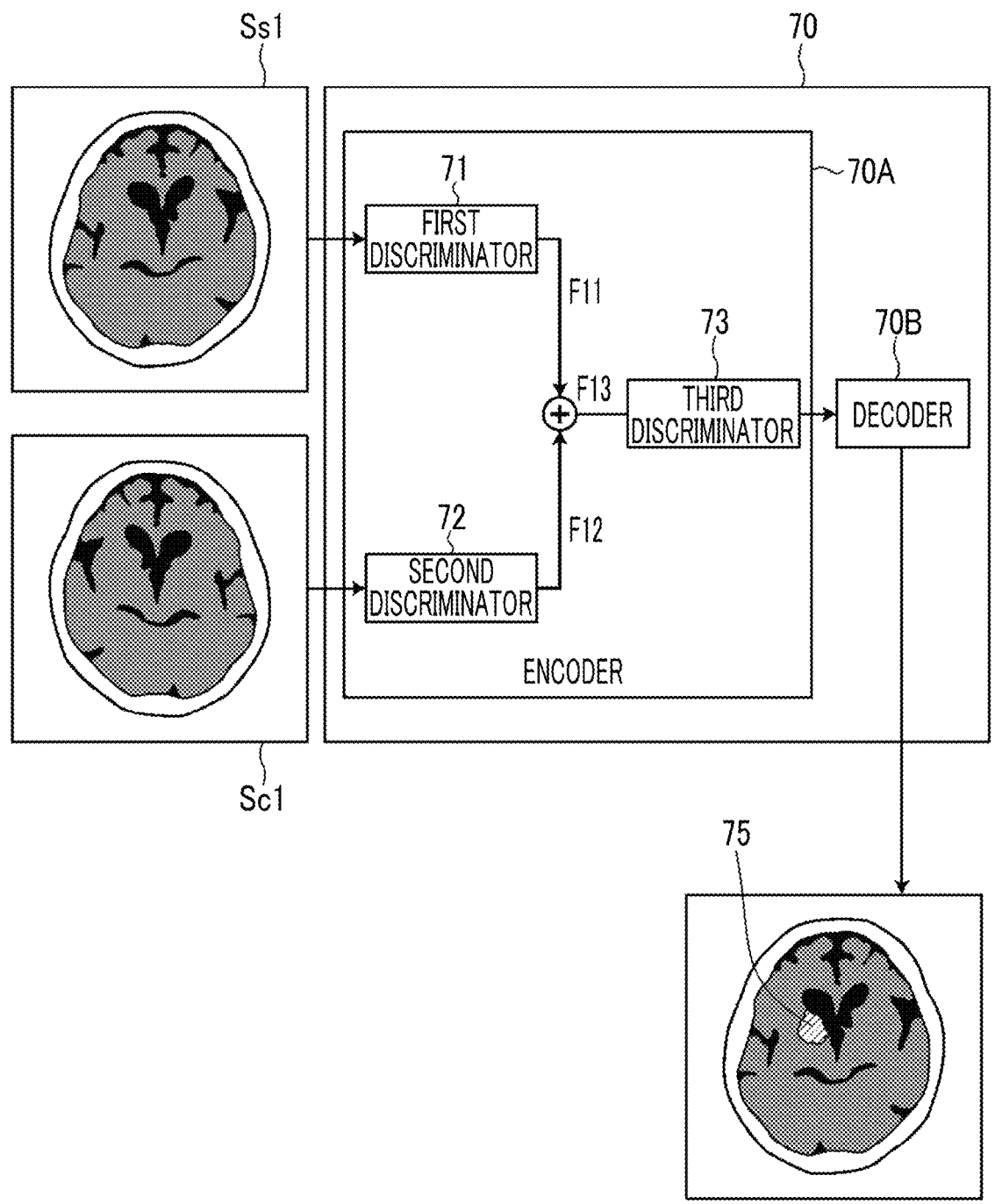
FIG. 21 is a conceptual diagram illustrating a process performed by a discrimination model of a discrimination unit together with a configuration of the discrimination model in a third embodiment.

FIG. 21 is a conceptual diagram illustrating a process performed by the discrimination model of the discrimination unit 26 together with a configuration of the discrimination model in the third embodiment. FIG. 21 illustrates only the normalized tomographic image Ss1 and the inverted tomographic image Sc1, but the same process is performed on the normalized tomographic image Ss2 and the inverted tomographic image Sc2. A discrimination model 70 illustrated in FIG. 21 consists of a CNN having an encoder 70A and a decoder 70B. The encoder 70A has a first discriminator 71, a second discriminator 72, and a third discriminator 73.

Similar to the first discriminator 61 in the second embodiment, the first discriminator 71 consists of a convolutional neural network having a plurality of processing layers including at least one of the convolutional layer or the pooling layer. The first discriminator 71 performs at least one of the convolution process or the pooling process in each processing layer to output a feature map F11 for the normalized tomographic image Ss1.

The second discriminator 72 consists of a convolutional neural network having a plurality of processing layers including at least one of the convolutional layer or the pooling layer. Parameters such as the weight of the kernel in each processing layer of the second discriminator 72 are common to those of the first discriminator 71. Accordingly, the first discriminator 71 and the second discriminator 72 are substantially the same discriminator. The second discriminator 72 performs at least one of the convolution process or the pooling process in each processing layer to output a feature map F12 for the inverted tomographic image Sc1.

The third discriminator 73 consists of a convolutional neural network having a plurality of processing layers including at least one of the convolutional layer or the pooling layer. The third discriminator 73 superimposes the feature map F11 output by the first discriminator 71 and the inverted feature map F12 output by the second discriminator 72 on each other to generate a superimposition map F13 in the first processing layer. In FIG. 21, for the description of superimposition, the first processing layer of the third discriminator 73 is indicated by a positive sign separately from the third discriminator 73. The third discriminator 73 discriminates the infarction region in the normalized tomographic images Ss1 and Ss2 on the basis of a superimposition map F13. Specifically, a process of specifying the infarction region is performed on the basis of the superimposition map F13.

The decoder 70B performs a process of classifying each pixel in the normalized tomographic images Ss1 and Ss2 into a pixel in the infarction region and a pixel that is not in the infarction region while increasing the resolution of the feature map, in which the infarction region is specified, such that the feature map has a resolution of the normalized tomographic images Ss1 and Ss2. In this manner, a discrimination result of an infarction region 75 in the normalized tomographic images Ss1 and Ss2 is output from the final layer of the decoder 70B which is the final layer of the discrimination model 70.

Figure 22:
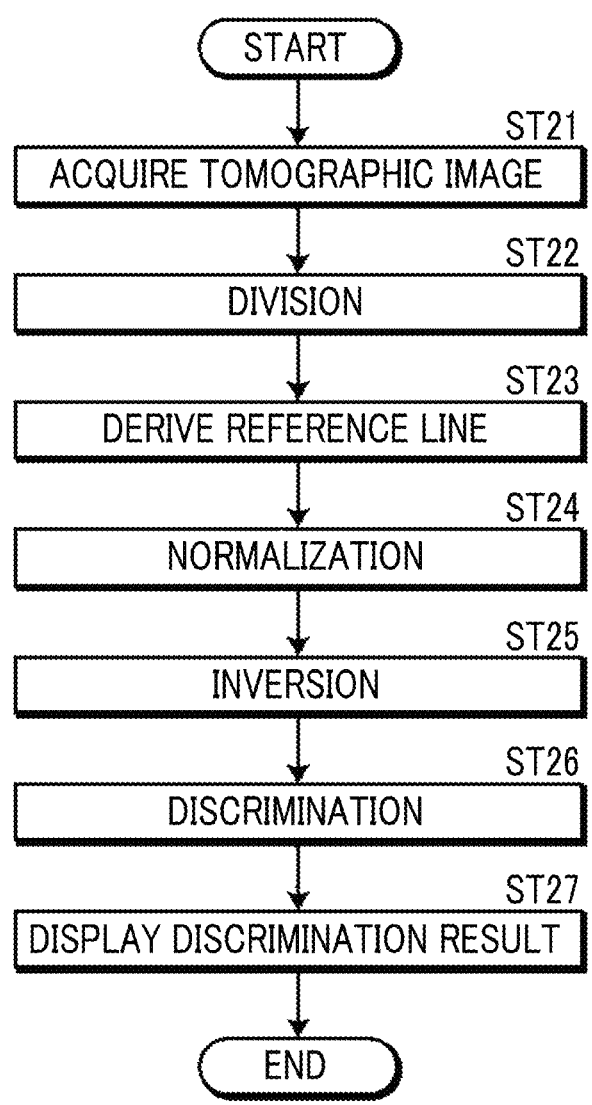
FIG. 22 is a flowchart illustrating a process performed in the third embodiment.

Next, the process performed in the third embodiment will be described. FIG. 22 is a flowchart illustrating the process performed in the third embodiment. First, the image acquisition unit 21 acquires the tomographic images S1 and S2 included in the brain image B0 (Step ST21). Next, the division unit 22 divides the brain included in the tomographic images S1 and S2 into a plurality of predetermined regions (Step ST22). The reference line derivation unit 23 derives the reference line BL of the brain on the basis of the plurality of divided regions in the tomographic images S1 and S2 (Step ST23). Further, the normalization unit 24 normalizes the position of the brain included in the tomographic images S1 and S2 (Step ST24). In this manner, the normalized tomographic images Ss1 and Ss2 are generated. Next, the inversion unit 25 inverts the normalized tomographic images Ss1 and Ss2 horizontally using the reference line BL as the reference (Step ST25). In this manner, the inverted tomographic images Sc1 and Sc2 are generated.

The discrimination unit 26 discriminates the disease region of the brain using the normalized tomographic images Ss1 and Ss2 and the inverted tomographic images Sc1 and Sc2 (Step ST26). Then, the display control unit 27 causes the display 14 to display the discrimination result (Step ST27), and the process is ended.

In the third embodiment, the third discriminator 73 may have the function of the decoder 70B. In this case, at the former stage of the third discriminator 73, a process is performed which discriminates the infarction region in the normalized tomographic images Ss1 and Ss2 on the basis of the superimposition map F13. Then, at the latter stage of the third discriminator 73, a process is performed which classifies each pixel in the normalized tomographic images Ss1 and Ss2 into a pixel in the infarction region and a pixel that is not in the infarction region while increasing the resolution of the feature map, in which the infarction region is specified, such that the feature map has a resolution of the normalized tomographic images Ss1 and Ss2.

In the third embodiment, the feature map F11 and the inverted feature map F12 are superimposed on each other in the first processing layer of the third discriminator 73, but the disclosure is not limited thereto. A difference map representing the difference between the feature map F11 and the inverted feature map F12 may be generated. In this case, the third discriminator 73 discriminates the infarction region in the normalized tomographic images Ss1 and Ss2 on the basis of the difference map.

Hereinafter, a fourth embodiment of the present disclosure will be described. Since a configuration of a medical image processing apparatus according to the fourth embodiment of the present disclosure is the same as that of the medical image processing apparatus 1 according to the first embodiment illustrated in FIG. 2, except that the process to be performed is different, the detailed description for the configuration is omitted.

Figure 23:
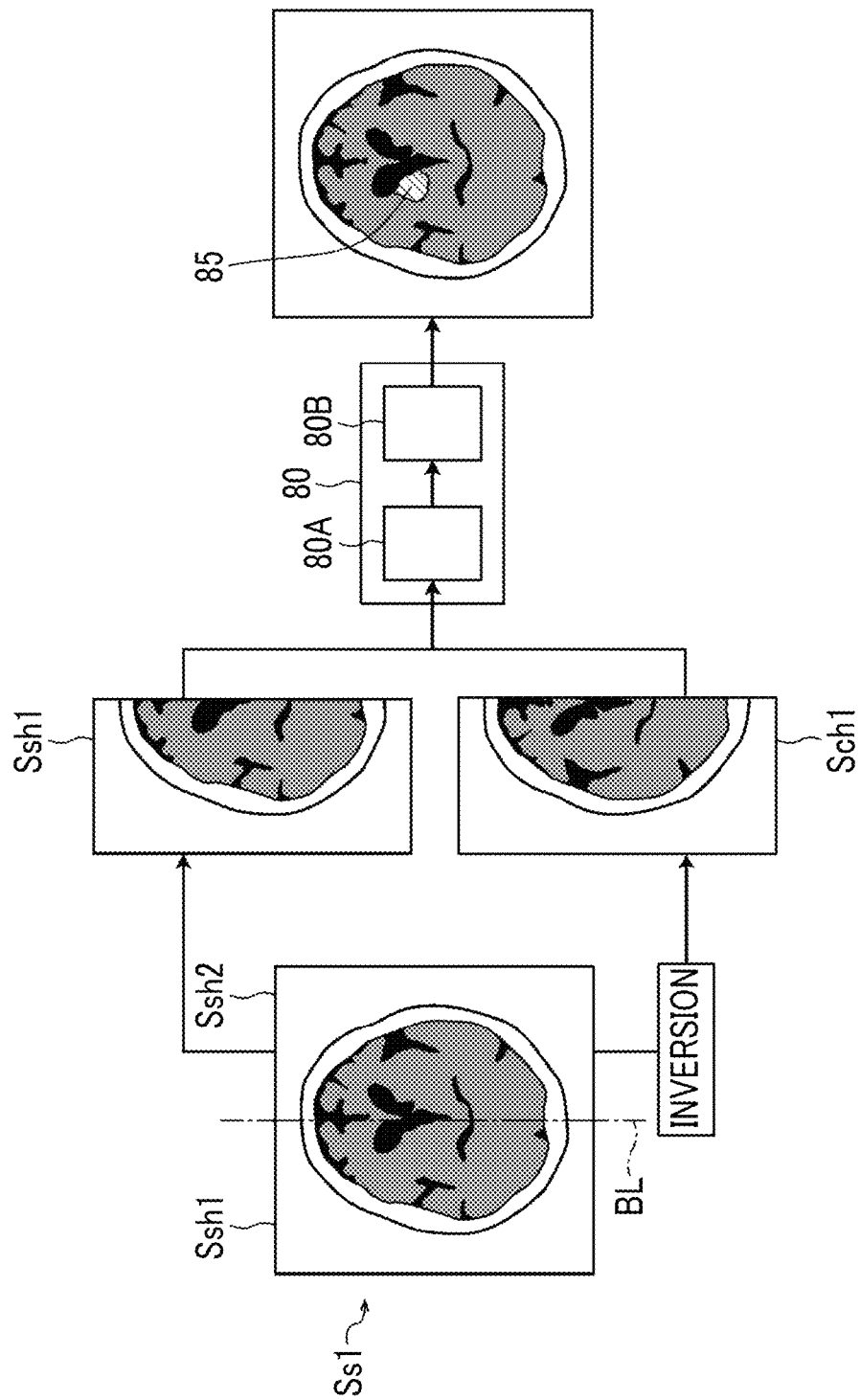
FIG. 23 is a conceptual diagram illustrating a process performed by a discrimination model of a discrimination unit together with a configuration of the discrimination model in a fourth embodiment.

FIG. 23 is a conceptual diagram illustrating a process to be performed together with a configuration of the discrimination model in the fourth embodiment. FIG. 23 illustrates only the normalized tomographic image Ss1, but the same process is performed on the normalized tomographic image Ss2. As illustrated in FIG. 23, in the fourth embodiment, the inversion unit 25 generates divided normalized tomographic images Ssh1 and Ssh2 by dividing the normalized tomographic image Ss1 into left and right using the reference line BL as the reference. The divided normalized tomographic images Ssh1 and Ssh2 have half the size of the normalized tomographic images Ss1 and Ss2. The divided normalized tomographic image Ssh1 indicates the right brain side, and the divided normalized tomographic image Ssh2 indicates the left brain side. Then, the inversion unit 25 generates a divided inverted tomographic image Sch1 by inverting any one of the divided normalized tomographic image Ssh1 or Ssh2 horizontally using the reference line BL as the reference. In FIG. 23, the divided inverted tomographic image Sch1 is generated by inverting the divided normalized tomographic image Ssh2 horizontally.

In the fourth embodiment, the discrimination unit 26 has a discrimination model 80 that discriminates the disease region (that is, the infarction region) of the brain using the divided normalized tomographic image and the divided inverted tomographic image. The discrimination model 80 illustrated in FIG. 23 has an encoder 80A and a decoder 80B. Similar to the encoder 30A in the first embodiment, the encoder 80A has a plurality of processing layers including at least one of the convolutional layer or the pooling layer. The encoder 80A performs the convolution process using various kernels on the basis of the difference in pixel values of the corresponding pixel positions of the divided normalized tomographic image Ssh1 and the divided inverted tomographic image Sch1 such that the infarction region can be detected so as to generate a feature map from the feature data obtained in the convolution process. Then, the encoder 80A specifies the infarction region in the feature map. Here, by using the difference in pixel values of the corresponding pixel positions of the two input images, the infarction region is detected using the symmetry using the reference line BL in the brain as the reference.

In the fourth embodiment, since the divided normalized tomographic image Ssh1 and the divided inverted tomographic image Sch1 are used, different labels are assigned to the infarction region detected in the divided normalized tomographic image Ssh1 and the infarction region detected in the divided inverted tomographic image Sch1. For example, a label of "1" is assigned to the infarction region detected in the divided normalized tomographic image Ssh1, that is, on the right brain side. Further, a label of "2" is assigned to the infarction region detected in the divided inverted tomographic image Sch1, that is, in the left brain side. A label of "0" is assigned to the region other than the infarction region.

Similar to the decoder 30B in the first embodiment, the decoder 80B has a plurality of convolutional layers and upsampling layers. The decoder 80B performs a process of classifying each pixel in the normalized tomographic images Ss1 and Ss2 into a pixel in the infarction region and a pixel that is not in the infarction region while increasing the resolution of the feature map output by the encoder 80A such that the feature map has a resolution of the normalized tomographic images Ss1 and Ss2. In this manner, a discrimination result of the infarction region in the normalized tomographic images Ss1 and Ss2 is output from the final layer of the decoder 80B which is the final layer of the discrimination model 80.

Here, in the encoder 80A of the fourth embodiment, the infarction region is specified by using the feature map for the image having half the size of the normalized tomographic images Ss1 and Ss2. Therefore, the feature map in which the infarction region is specified is upsampled in the decoder 80B, and it is necessary for the feature map to have the same size as the normalized tomographic image Ss1 in a case where the infarction region is finally specified in the normalized tomographic images Ss1 and Ss2. Accordingly, the decoder 80B upsamples the feature map to half the resolution of the normalized tomographic images Ss1 and Ss2 in the processing layer at the former stage. Then, the size of the feature map is made the same as the normalized tomographic images Ss1 and Ss2 by interpolating the region according to the label of the detected infarction region in the upsampled feature map. Further, the decoder 80B generates the feature map in which the region is interpolated and specifies the infarction region in the normalized tomographic images Ss1 and Ss2, in the processing layer at the latter stage.

Figure 24:
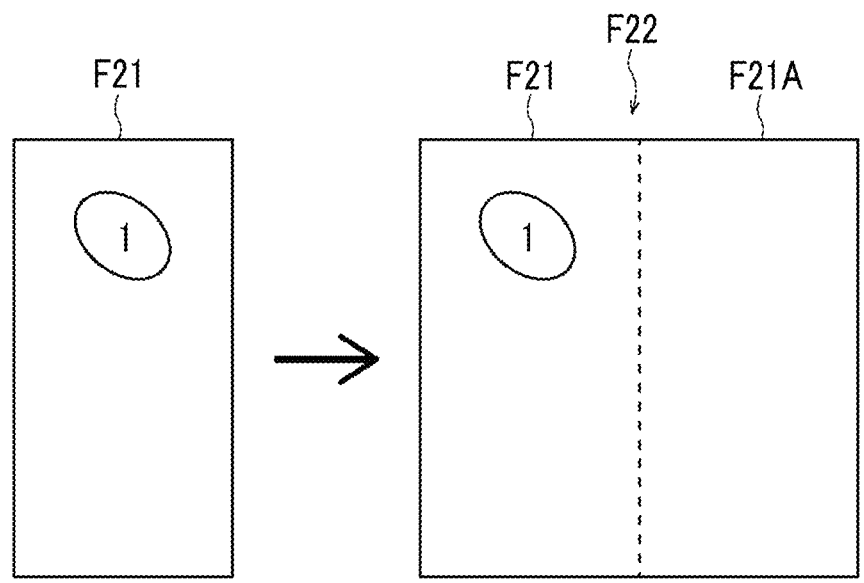
FIG. 24 is a diagram for describing interpolation of a region for a feature map.

FIGS. 24 to 27 are diagrams for describing the interpolation of the region for the feature map. In FIGS. 24 to 27, feature maps F21, F23, F25, and F27 that are upsampled to the same resolution as the divided normalized tomographic images Ssh1 and Ssh2 are illustrated. As illustrated in FIG. 24, in a case where the label of the infarction region detected in the feature map F21 is "1", the infarction region is detected on the right brain side. Therefore, as illustrated in FIG. 24, the decoder 80B generates the feature map F22 having the same size as the normalized tomographic images Ss1 and Ss2 by interpolating a region F21A which has the same size as the feature map F21 and in which a label of "0" is assigned to the entire region, in a region on the right side of the feature map F21.

Figure 25:
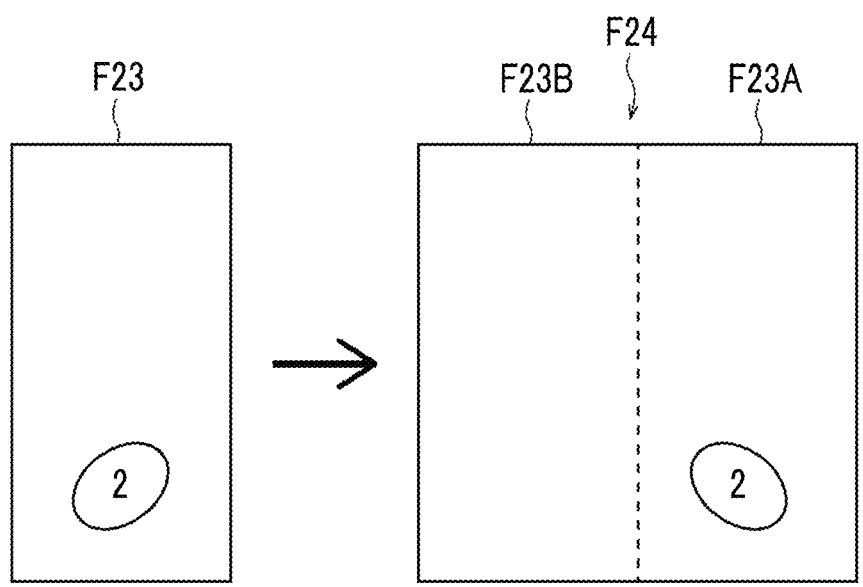
FIG. 25 is a diagram for describing interpolation of a region for a feature map.

As illustrated in FIG. 25, in a case where the label of the infarction region detected in the feature map F23 is "2", the infarction region is detected on the left brain side. Therefore, as illustrated in FIG. 25, the decoder 80B generates a feature map F23A by inverting the infarction region having a label of "2" included in the feature map F23 horizontally using the right side of the feature map F23 as the reference. Then, a feature map F24 having the same size as the normalized tomographic images Ss1 and Ss2 is generated by interpolating a region F23B which has the same size as the feature map F23A and in which a label of "0" is assigned to the entire region, in a region on the left side of the inverted feature map F23A.

Figure 26:
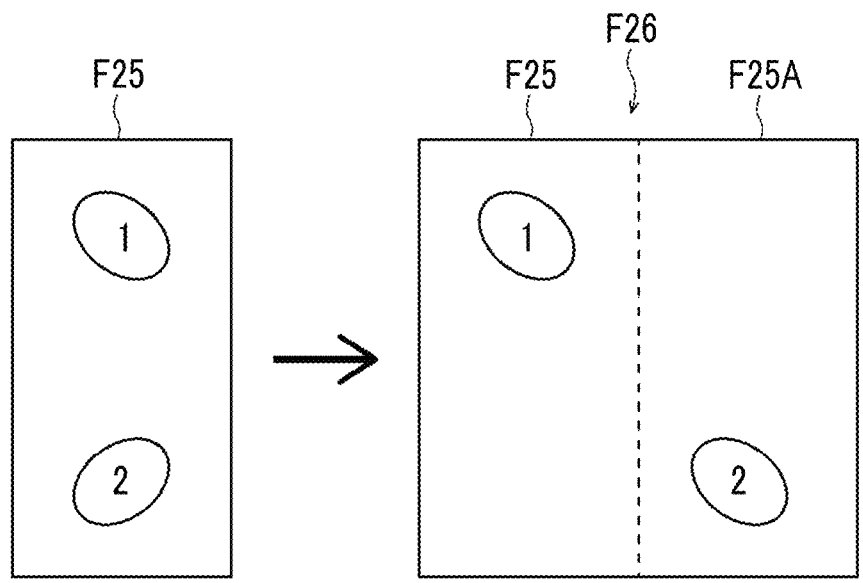
FIG. 26 is a diagram for describing interpolation of a region for a feature map.

As illustrated in FIG. 26, in a case where two infarction regions are detected in the feature map F25 and the labels of the two detected infarction regions are respectively "1" and "2", the infarction region is detected in both the left and right brains. Therefore, the decoder 80B interpolates a region F25A which has the same size as the feature map F25 and in which a label of "0" is assigned to the entire region, in a region on the right side of the feature map F25. Further, the decoder 80B inverts the infarction region having a label of "2" included in the feature map F25 horizontally using the right side of the feature map F25 as the reference, and assigns the label to the interpolated region F25A. In this manner, as illustrated in FIG. 26, the decoder 80B generates a feature map F26 having the same size as the normalized tomographic images Ss1 and Ss2.

Figure 27:
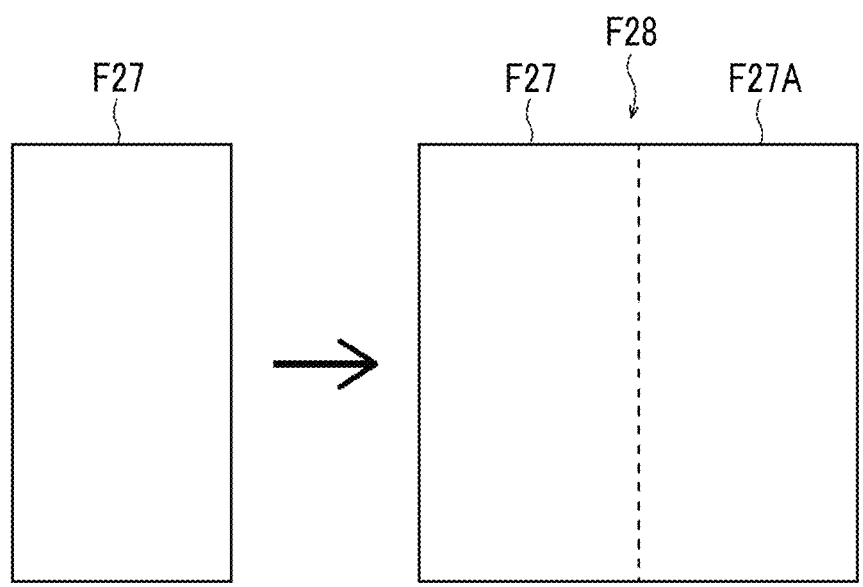
FIG. 27 is a diagram for describing interpolation of a region for a feature map.

In a case where there is no detected infarction region in the feature map F27 as illustrated in FIG. 27, the decoder 80B generates a feature map F28 having the same size as the normalized tomographic images Ss1 and Ss2 by interpolating a region F27A which has the same size as the feature map F27 and in which a label of "0" is assigned to the entire region, in a region on the left side of the feature map F27, as illustrated in FIG. 27.

Figure 28:
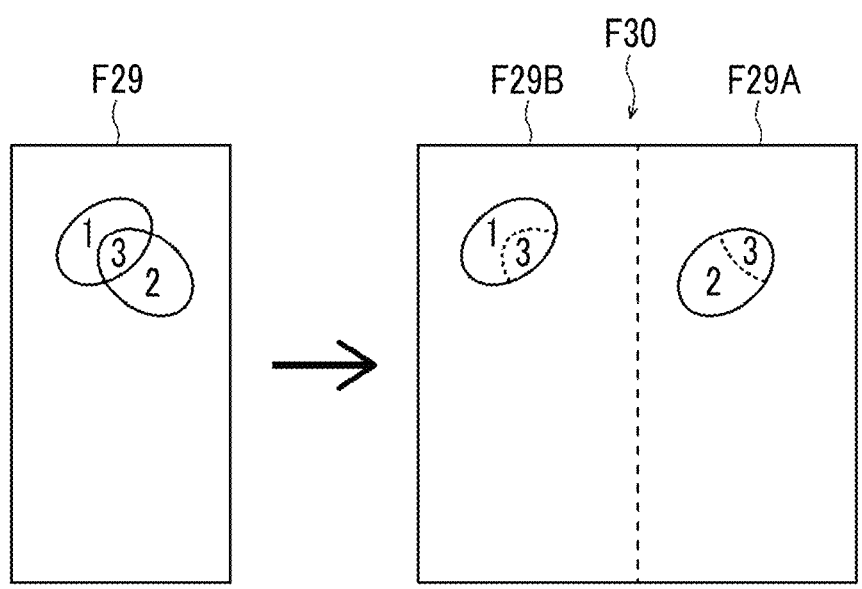
FIG. 28 is a diagram for describing interpolation of a region for a feature map.

In a case where the infarction region is detected in both the left and right brains, the region having a label of "1" and the region having a label of "2" may overlap each other in a feature map F29 as illustrated in FIG. 28. In this case, in the encoder 80A, a label of "3" is assigned to a region where the region having a label of "1" and the region having a label of "2" overlap each other. Then, the decoder 80B interpolates a region F29A which has the same size as the feature map F29 and in which a label of "0" is assigned to the entire region, in a region on the right side of the feature map F29. Further, the decoder 80B inverts the infarction region having labels of "2" and "3" included in the feature map F29 horizontally using the right side of the feature map F29 as the reference while deleting the region having a label of "2" included in the feature map F29, and assigns the labels to the interpolated region F29A. In this manner, as illustrated in FIG. 28, the decoder 80B generates a feature map F30 which consists of a feature map F29B obtained by deleting the region having a label of "2" in the feature map F29, and a feature map F29A, and has the same size as the normalized tomographic images Ss1 and Ss2.

Also in the third embodiment, similar to the fourth embodiment, the infarction region of the brain may be detected using the divided normalized tomographic image and the divided inverted tomographic image instead of the normalized tomographic images Ss1 and Ss2 and the inverted tomographic images Sc1 and Sc2 in the first embodiment.

Figure 29:
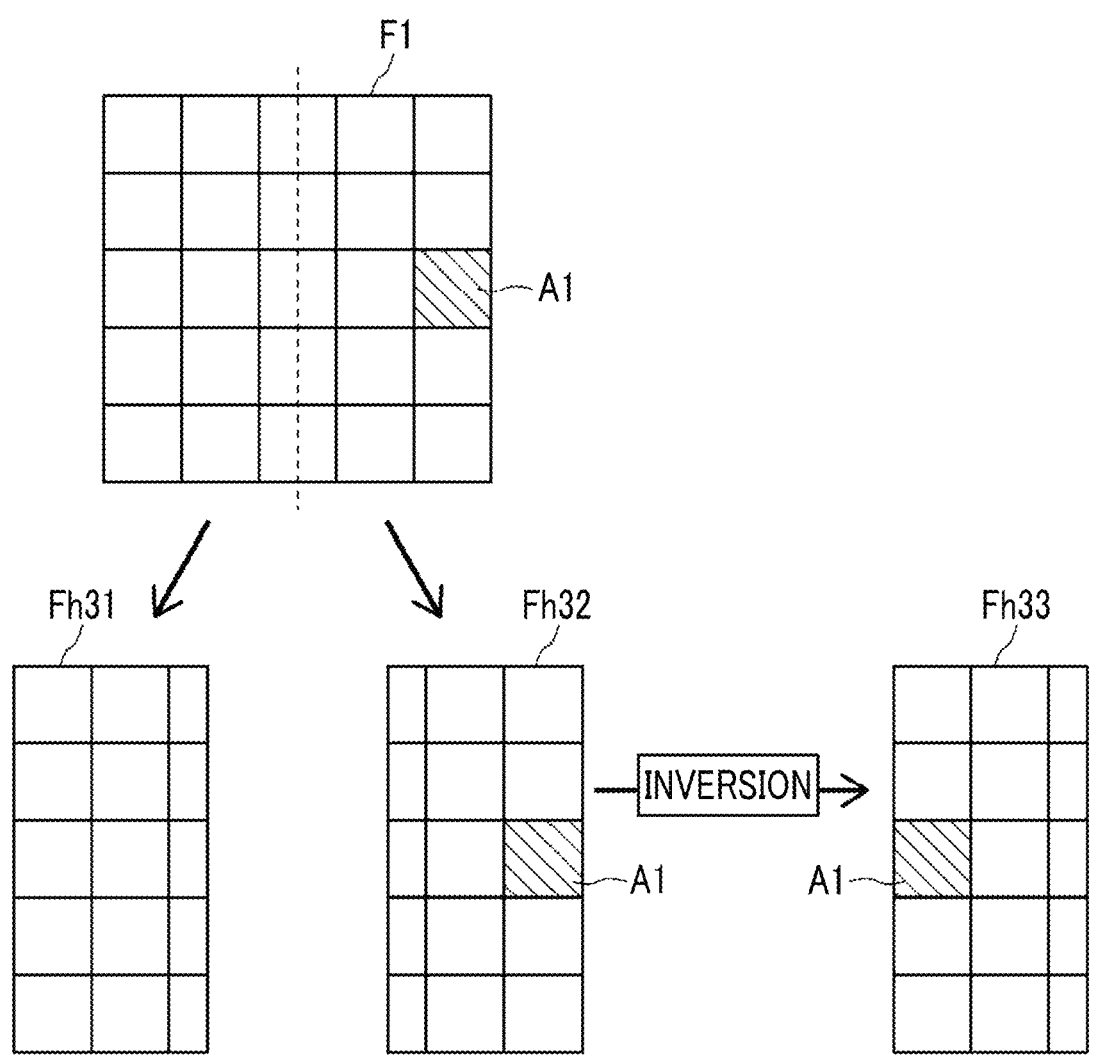
FIG. 29 is a diagram for describing a process in a case where a method in the fourth embodiment is applied to the second embodiment.

The same method as in the fourth embodiment can be applied to the second embodiment. In a case where the same method as in the fourth embodiment is applied to the second embodiment, as illustrated in FIG. 29, the feature map F1 output by the first discriminator 61 is divided using the axis of symmetry corresponding to the reference line BL as the reference so that divided feature maps Fh31 and Fh32 are generated. It is assumed that the divided feature map Fh31 indicates the right brain side, and the divided feature map Fh32 indicates the left brain side. The second discriminator 62 generates a divided inverted feature map Fh33 by inverting any one of the divided feature maps (the divided feature map Fh32 in FIG. 29) horizontally. Then, the third discriminator 63 generates a superimposition map or a difference map from the divided feature map Fh31 and the divided inverted feature map Fh33, and detects the infarction region in both the right brain side and the left brain side using the superimposition map or the difference map. The decoder 60B may generate a feature map having the same size as the normalized tomographic images Ss1 and Ss2 by interpolating a region in the same manner as in the decoder 80B in the fourth embodiment, and may output a discrimination result of the infarction region in the normalized tomographic images Ss1 and Ss2.

In the fourth embodiment, the divided inverted tomographic image Sch1 is generated from the divided normalized tomographic image Ssh2 on the left brain side, but the divided inverted tomographic image may be generated from the divided normalized tomographic image Ssh1 on the right brain side. In this case, the divided inverted tomographic image generated from the divided normalized tomographic image Ssh1 on the right brain side and the divided normalized tomographic image Ssh2 are input to the discrimination model 80, and a discrimination result of the infarction region in the normalized tomographic images Ss1 and Ss2 is output.

In each embodiment described above, in the normalization unit 24, the normalized tomographic images Ss1 and Ss2 are generated by normalizing the position of the brain included in the tomographic images S1 and S2 on the basis of the reference line BL derived by the reference line derivation unit 23, but the disclosure is not limited thereto. The method is not limited to the method using the reference line BL as long as the normalized medical image can be generated by normalizing the position of the structure included in the medical image such as the tomographic images S1 and S2. That is, the normalization unit 24 may generate the normalized medical image by normalizing the position of the structure (brain) included in the medical image (tomographic images S1 and S2) without being on the basis of the reference line derived by the reference line derivation unit 23. For example, the tomographic images S1 and S2 are displayed on the display 14, and the normalized tomographic images Ss1 and Ss2 may be generated on the basis of an operation of the operator to normalize the position of the brain included in the tomographic images S1 and S2 using the input device 15. The normalization unit 24 may generate the normalized tomographic images Ss1 and Ss2 in which the position of the brain included in the tomographic images S1 and S2 is normalized by aligning the standard image of the brain with the defined reference line, with the tomographic images S1 and S2.

Figure 30:
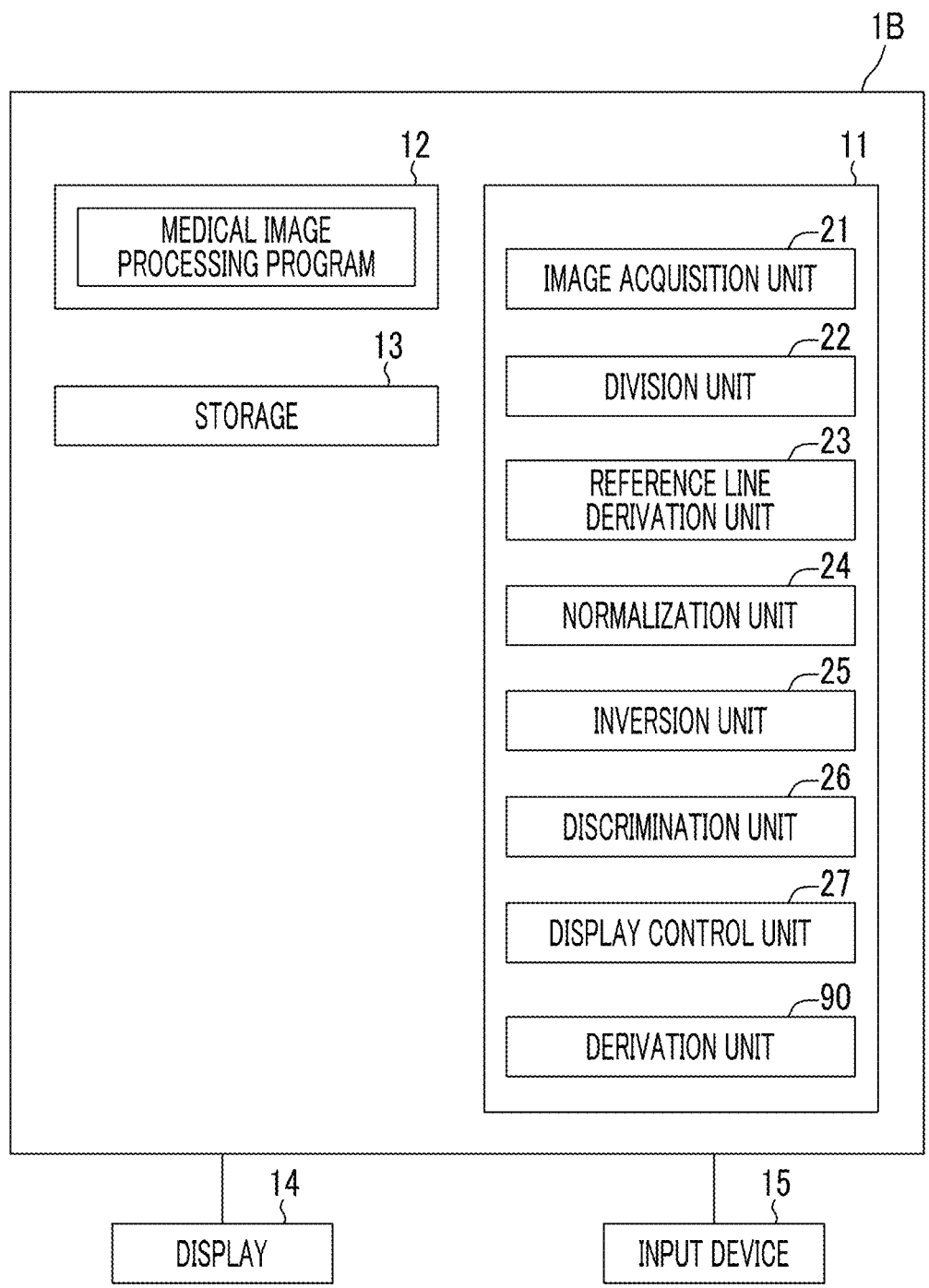
FIG. 30 is a diagram illustrating a schematic configuration of a medical image processing apparatus according to the first embodiment in which a derivation unit is provided.

In each embodiment described above, the operator assigns a check mark to the ASPECTS on the discrimination result display screen, but the disclosure is not limited thereto. For example, as in a medical image processing apparatus 1B illustrated in FIG. 30, a derivation unit 90 that derives the ASPECTS may be provided to the medical image processing apparatus 1 according to the first embodiment. The derivation unit 90 determines which region for deriving the ASPECTS in the normalized tomographic images Ss1 and Ss2 includes the detected infarction region. That is, the derivation unit 90 determines which region among the regions of C, I, L, IC, and M1 to M3 of each of the left and right brains in the normalized tomographic image Ss1 and the regions of M4 to M6 of each of the left and right brains in the normalized tomographic image Ss2 includes the infarction region. Specifically, in a case where the infarction region is included in a region for deriving the ASPECTS in a predetermined ratio or more, it is determined that the region is the infarction region. Then, the derivation unit 90 assigns the check mark to the ASPECTS 55 illustrated in FIG. 13 for the region determined to be the infarction region.

Here, the predetermined ratio can be appropriately set according to the degree of strictness of the determination. For example, the predetermined ratio can be 10%, but may be 20% or 30%. Further, in a case where the infarction region is included in a region for deriving the ASPECTS even a little, the region may be determined as the infarction region.

The derivation unit 90 may be provided not only in the first embodiment but also in any of the second embodiment to the fourth embodiment.

Further, in each embodiment described above, the CNN is used as the discrimination model, but the disclosure is not limited thereto. As long as the neural network includes a plurality of processing layers, a deep neural network (DNN), a recurrent neural network (RNN), U-Net or the like can be used. Further, as the neural network, a neural network using Mask Regions with CNN features (R-CNN) ("Mask R-CNN", Kaiming He et al., arXiv, 2018) may be used. Hereinafter, the Mask R-CNN will be described.

FIG. 31 is a schematic configuration diagram of the Mask R-CNN. FIG. 31 illustrates an example in which the Mask R-CNN is applied as the discrimination model 30 in the first embodiment. As illustrated in FIG. 31, a Mask R-CNN 100 includes a convolutional layer 101 that generates a feature map F40 by extracting a feature quantity from the input image; a Region Proposal Network (RPN) 102 that specifies candidate regions for the infarction region in the feature map F40; a classification network 103 that cuts out the feature map F40 on the basis of the candidate regions for the infarction region, and outputs a class of the candidate region using the cut-out feature map and coordinate information of the candidate region in the normalized tomographic images Ss1 and Ss2; and a segmentation 104 that specifies the infarction region in the normalized tomographic images Ss1 and Ss2 using a pixel level.

Similar to the encoder in each embodiment described above, the convolutional layer 101 performs the convolution process using various kernels on the input normalized tomographic images Ss1 and Ss2 and the input inverted tomographic images Sc1 and Sc2, and outputs the feature map F40 consisting of feature data obtained by the convolution process.

In the RPN 102, a rectangular region called an anchor having a plurality of types of aspect ratios and sizes is defined in advance. In the RPN 102, the plurality of types of anchors are applied to each pixel position of the feature map F40, and an anchor with the highest overlap rate with an object candidate included in the normalized tomographic images Ss1 and Ss2 is selected. In the RPN 102, a process of regressing (that is, deforming and moving) the anchor so as to coincide with a rectangle (ground truth box) surrounding the object candidate using the selected anchor is performed on all the pixels of the feature map F40, and the position and size of the anchor regressed to coincide with the ground truth box are output from the RPN 102 as a candidate region A10 of the infarction region in the input normalized tomographic images Ss1 and Ss2. The candidate region A10 is a rectangular region surrounding the infarction region.

The classification network 103 consists of fully connected layers, and performs classification of the candidate region A10 in the normalized tomographic images Ss1 and Ss2 and derivation of the coordinate information of the candidate region A10 in the normalized tomographic images Ss1 and Ss2 on the basis of the candidate region A10 and the feature map F40.

The segmentation 104 consists of a fully convolutional network (FCN), segments the infarction region in the normalized tomographic images Ss1 and Ss2 by specifying the pixel which is the infarction region in the candidate region A10 on the basis of the candidate region A10 and the feature map F40. FIG. 31 illustrates a segmented state of an infarction region 105 in the normalized tomographic image Ss1.

As described above, the infarction region in the normalized tomographic images Ss1 and Ss2 can be specified by using the Mask R-CNN 100 as the discrimination model 30 in the first embodiment.

The Mask R-CNN can be used as the discrimination model 60 in the second embodiment. In this case, in the Mask R-CNN, only the normalized tomographic images Ss1 and Ss2 are input, and the feature map of the normalized tomographic images Ss1 and Ss2 and the inverted feature map thereof are generated in the convolutional layer 101. Further, in the convolutional layer 101, the superimposition map of the feature map and the inverted feature map thereof is generated and output. In the convolutional layer 101, convolution and pooling are further performed on the superimposition map, and the superimposition map to which the convolution and pooling have been performed may be output. In this case, in the RPN 102, the map output by the convolutional layer 101 is input, and the candidate region A10 of the infarction region in the normalized tomographic images Ss1 and Ss2 is output. Further, in the classification network 103 and the segmentation 104, the map output by the convolutional layer 101 and the candidate region A10 output by the RPN 102 are input, and the infarction region 105 in the normalized tomographic images Ss1 and Ss2 is specified.

The Mask R-CNN can be used as the discrimination model 70 in the third embodiment. In this case, in the Mask R-CNN 100, each of the normalized tomographic images Ss1 and Ss2 and the inverted tomographic images Sc1 and Sc2 is input, the feature map for the normalized tomographic images Ss1 and Ss2 and the feature map for the inverted tomographic images Sc1 and Sc2 (hereinafter, referred to as inverted feature map) are generated in the convolutional layer 101, and a superimposition map or a difference map of the feature map and the inverted feature map thereof is generated and output. In the convolutional layer 101, convolution and pooling are further performed on the superimposition map or the difference map, and the superimposition map of the difference map to which the convolution and pooling have been performed may be output. In this case, in the RPN 102, the map output by the convolutional layer 101 is input, and the candidate region A10 of the infarction region in the normalized tomographic images Ss1 and Ss2 is output. Further, in the classification network 103 and the segmentation 104, the map output by the convolutional layer 101 and the candidate region A10 output by the RPN 102 are input, and the infarction region 105 in the normalized tomographic images Ss1 and Ss2 is specified.

The Mask R-CNN can be used as the discrimination model 80 in the fourth embodiment. In this case, in the Mask R-CNN 100, each of the divided normalized tomographic images Ssh1 and Ssh2 and the divided inverted tomographic images Sch1 and Sch2 is input, and a feature map focusing on the difference in pixel values of the corresponding pixel positions of the divided normalized tomographic images Ssh1 and Ssh2 and the divided inverted tomographic images Sch1 and Sch2 is output from the convolutional layer 101. In this case, in the RPN 102, the feature map output by the convolutional layer 101 is input, and the candidate region A10 of the infarction region in the normalized tomographic images Ss1 and Ss2 is output. Further, in the classification network 103 and the segmentation 104, the feature map output by the convolutional layer 101 and the candidate region A10 output by the RPN 102 are input, and the infarction region 105 in the normalized tomographic images Ss1 and Ss2 is specified. In this case, the feature map is interpolated to have the same size as the normalized tomographic images Ss1 and Ss2 in the processing layer before the final layer of the classification network 103 and the segmentation 104.

As described above, the same method as that in the fourth embodiment can be applied even in the second embodiment, and as the discrimination model used in such a case, the Mask R-CNN can be used. As described above, the same method as that in the fourth embodiment can be applied even in the third embodiment, and as the discrimination model used in such a case, the Mask R-CNN can be used.

In each embodiment described above, the tomographic images S1 and S2 are divided into the plurality of regions for determining the ASPECTS, but the disclosure is not limited thereto. For example, the tomographic images S1 and S2 may be divided into the plurality of regions by a method of dividing the brain into functional regions, such as Brodmann's brain map.

In the embodiment described above, the reference line BL of the brain included in the two-dimensional tomographic images S1 and S2 is derived, but the disclosure is not limited thereto. The three-dimensional brain image B0 may be divided into a plurality of regions, and a reference plane corresponding to a median plane of the brain included in the three-dimensional brain image B0 may be derived on the basis of the plurality of regions.

In each embodiment described above, the discrimination result of the normalized tomographic images Ss1 and Ss2 is displayed on the discrimination result display screen 50, but the disclosure is not limited thereto. The tomographic images S1 and S2 before normalization may be displayed on the discrimination result display screen 50. In this case, a mask for specifying the infarction region may be displayed on the tomographic images S1 and S2 by aligning the normalized tomographic images Ss1 and Ss2 including the discrimination result with the tomographic images S1 and S2.

In each embodiment described above, in the reference line derivation unit 23 and the normalization unit 24, a new normalized tomographic image may be generated by performing again the derivation of the centroids of the left brain and the right brain, the derivation of the reference line, and the normalization on the normalized tomographic images Ss1 and Ss2 generated by performing the derivation of the centroids of the left brain and the right brain, the derivation of the reference line, and the normalization. In this case, the derivation of the centroids of the left brain and the right brain, the derivation of the reference line, and the normalization may be further repeatedly performed on the new normalized tomographic image. In this manner, since the accuracy of the normalization can be improved, it is possible to more accurately discriminate the infarction region.

In the second embodiment, the second discriminator 62 of the discrimination model 60 generates the inverted feature map F2, and the third discriminator 63 of the discrimination model 60 generates the superimposition map of the feature map F1 and the inverted feature map F2 to discriminate the infarction region, but the disclosure is not limited thereto. The third discriminator 63 may generate the difference map by deriving the difference in corresponding pixels of the feature map F1 and the inverted feature map F2, and discriminate the infarction region on the basis of the feature map F1 and the difference map. Even in a case where the Mask R-CNN is used as the discrimination model 60 in the second embodiment, the difference map of the feature map and the inverted feature map thereof may be generated in the convolutional layer 101. In this case, in the RPN 102, the difference map or a map obtained by further performing the convolution and the pooling on the difference map is input.

The first discriminator 61, the second discriminator 62, and the third discriminator 63 included in the discrimination model 60 in the second embodiment may not be the same type of neural network. For example, the first discriminator 61 and the second discriminator 62 may be the convolutional neural network, and the third discriminator 63 may be the recurrent neural network instead of the CNN.

The first discriminator 71, the second discriminator 72, and the third discriminator 73 included in the discrimination model 70 in the third embodiment may not be the same type of neural network. For example, the first discriminator 71 and the second discriminator 72 may be the convolutional neural network, and the third discriminator 73 may be the recurrent neural network instead of the CNN.

In each embodiment described above, the infarction region of the brain is discriminated, but the disclosure is not limited thereto, and a bleeding region of the brain may be discriminated. In this case, the discrimination model is trained to discriminate the bleeding region of the brain.

Further, in each embodiment described above, the CT image is used as the brain image B0 and the tomographic images S1 and S2, but the disclosure is not limited thereto, and other medical images such as the MM image and the PET image may be used.

Further, in each embodiment described above, the brain image is used as the medical image, but the disclosure is not limited thereto. For example, the technique of the present disclosure can be applied even in a case of discriminating the disease region in the medical image including a pair or a plurality of pairs of structures present in an axisymmetric manner such as lungs, kidneys, eyeballs, and ears.

In each embodiment described above, the following various processors can be used as the hardware structure of processing units executing various processes such as the image acquisition unit 21, the division unit 22, the reference line derivation unit 23, the normalization unit 24, the inversion unit 25, the discrimination unit 26, the display control unit 27, the discrimination unit 29, and the derivation unit 90. The various processors include, for example, a programmable logic device (PLD) that is a processor of which the circuit configuration can be changed after manufacture, such as a field-programmable gate array (FPGA), and a dedicated electric circuit that is a processor having a dedicated circuit configuration designed to execute a specific process, such as an application specific integrated circuit (ASIC), in addition to the CPU that is a general-purpose processor which executes software (programs) to function as various processing units as described above.

One processing unit may be configured by one of the various processors or a combination of the same or different kinds of two or more processors (for example, a combination of a plurality of FPGAs or a combination of a CPU and an FPGA). In addition, a plurality of processing units may be configured by one processor.

As an example where a plurality of processing units are configured by one processor, first, there is a form where one processor is configured by a combination of one or more CPUs and software as typified by a computer, such as a client and a server, and this processor functions as a plurality of processing units. Second, there is a form where a processor fulfilling the functions of the entire system including a plurality of processing units by means of one integrated circuit (IC) chip as typified by a system on chip (SoC) or the like is used. In this manner, various processing units are configured by using one or more of the above-described various processors as hardware structures.

In addition, specifically, an electric circuit (circuitry) obtained by combining circuit elements, such as semiconductor elements, can be used as the hardware structure of the various processors.

What is claimed is:

1. A medical image processing apparatus comprising at least one processor, wherein the processor is configured to:
divide an axisymmetric structure in a medical image including the structure into a plurality of predetermined regions;
derive a reference line of the structure on the basis of the plurality of divided regions;
generate a normalized medical image by normalizing a position of the structure included in the medical image on the basis of the reference line;
generate an inverted image by inverting the normalized medical image using the reference line as a reference; and
acquire a discrimination result of a disease region of the structure according to a difference in pixel values of corresponding pixel positions in the normalized medical image and the inverted image.

2. The medical image processing apparatus according to claim 1, wherein the processor is configured to discriminate the disease region by a discrimination model that outputs the discrimination result of the disease region of the structure in a case where the normalized medical image and the inverted image are input.

3. The medical image processing apparatus according to claim 2,
wherein in a case where the normalized medical image and the inverted image are input, the discrimination model generates at least one feature map for the normalized medical image and the inverted image, and outputs the discrimination result of the disease region of the structure using the at least one feature map.

4. The medical image processing apparatus according to claim 2,
wherein the discrimination model generates at least one feature map for each of the normalized medical image and the inverted image, and outputs the discrimination result of the disease region of the structure using the at least one feature map for the normalized medical image and the at least one feature map for the inverted image.

5. The medical image processing apparatus according to claim 1, wherein the processor is configured to discriminate the disease region by a discrimination model that generates an inverted image of the normalized medical image and outputs a discrimination result of the disease region of the structure in a case where the normalized medical image is input.

6. The medical image processing apparatus according to claim 5,
wherein in a case where the normalized medical image is input, the discrimination model generates a at least one feature map from the normalized medical image, generates at least one inverted feature map obtained by inverting the at least one feature map using an axis of symmetry corresponding to the reference line as the reference, and outputs a discrimination result of the disease region of the structure using the at least one feature map and the at least one inverted feature map.

7. The medical image processing apparatus according to claim 2,
wherein the discrimination model consists of a neural network having at least one processing layer.

8. The medical image processing apparatus according to claim 1, wherein the processor is further configured to cause a display to display a discrimination result.

9. The medical image processing apparatus according to claim 1,
wherein the structure is a brain, and the disease region is an infarction region.

10. The medical image processing apparatus according to claim 9,
wherein the plurality of predetermined regions are regions for deriving ASPECTS.

11. The medical image processing apparatus according to claim 10, wherein the processor is further configured to:
derive the ASPECTS using the infarction region and the region for deriving the ASPECTS.

12. A medical image processing method comprising:
dividing an axisymmetric structure in a medical image including the structure into a plurality of predetermined regions;
deriving a reference line of the structure on the basis of the plurality of divided regions;
generating a normalized medical image by normalizing a position of the structure included in the medical image on the basis of the reference line;
generating an inverted image by inverting the normalized medical image using the reference line as a reference; and
acquiring a discrimination result of a disease region of the structure according to a difference in pixel values of corresponding pixel positions in the normalized medical image and the inverted image.

13. A non-transitory computer-readable storage medium that stores a medical image processing program causing a computer to execute:
a procedure of dividing an axisymmetric structure in a medical image including the structure into a plurality of predetermined regions;
a procedure of deriving a reference line of the structure on the basis of the plurality of divided regions;
a procedure of generating a normalized medical image by normalizing a position of the structure included in the medical image on the basis of the reference line;
a procedure of generating an inverted image by inverting the normalized medical image using the reference line as a reference; and
a procedure of acquiring a discrimination result of a disease region of the structure according to a difference in pixel values of corresponding pixel positions in the normalized medical image and the inverted image.

* * * * *